United States Patent [19]
Lindall

[11] Patent Number: 5,470,307
[45] Date of Patent: Nov. 28, 1995

[54] CATHETER SYSTEM FOR CONTROLLABLY RELEASING A THERAPEUTIC AGENT AT A REMOTE TISSUE SITE

[76] Inventor: Arnold W. Lindall, 1150 Nordic Ave. North, P.O. Box 187, Stillwater, Minn. 55082

[21] Appl. No.: 214,051

[22] Filed: Mar. 16, 1994

[51] Int. Cl.[6] .................................................. A61M 1/00
[52] U.S. Cl. ...................... 604/20; 604/265; 604/890.1; 604/28; 128/634
[58] Field of Search ...................... 604/20, 28, 264–266, 604/890.1, 891.1, 892.1, 92, 93, 95–96, 83, 113, 51–53, 57, 48–49; 128/633–634, 898, DIG. 3; 606/7, 194; 607/92

[56] References Cited

U.S. PATENT DOCUMENTS

| | | |
|---|---|---|
| 2,883,986 | 4/1959 | De Luca et al. . |
| 3,435,826 | 4/1969 | Fogarty . |
| 3,467,101 | 9/1969 | Fogarty et al. . |
| 3,570,476 | 3/1971 | Gregg . |
| 3,901,829 | 8/1975 | Slingluff et al. . |
| 4,062,746 | 12/1977 | Rich et al. . |
| 4,156,066 | 5/1979 | Gould . |
| 4,156,067 | 5/1979 | Gould . |
| 4,195,637 | 4/1980 | Gruntzig et al. . |
| 4,271,839 | 6/1981 | Fogarty et al. . |
| 4,289,128 | 9/1981 | Rusch . |
| 4,323,071 | 4/1982 | Simpson et al. . |
| 4,359,453 | 11/1982 | Gordon . |
| 4,479,497 | 10/1984 | Fogarty et al. . |
| 4,531,943 | 7/1985 | Van Tassel et al. . |
| 4,545,390 | 10/1985 | Leary . |
| 4,554,929 | 11/1985 | Samson et al. . |
| 4,571,240 | 2/1986 | Samson et al. . |
| 4,573,966 | 3/1986 | Weikl et al. . |
| 4,581,017 | 4/1986 | Sahota . |
| 4,582,181 | 4/1986 | Samson . |
| 4,597,755 | 7/1986 | Samson et al. . |
| 4,610,241 | 9/1986 | Gordon . |
| 4,616,648 | 10/1986 | Simpson . |
| 4,702,252 | 10/1987 | Brooks et al. . |
| 4,743,673 | 5/1988 | Johnston et al. . |
| 4,748,982 | 6/1988 | Horzewski et al. . |
| 4,762,129 | 8/1988 | Bonzel . |
| 4,771,130 | 9/1988 | Cohen . |
| 4,799,479 | 1/1989 | Spears . |
| 4,807,620 | 2/1989 | Strul et al. . |
| 4,824,436 | 4/1989 | Wolinsky . |
| 4,835,258 | 5/1989 | Hollenberg et al. . |
| 4,846,171 | 7/1989 | Kauphusman et al. . |
| 4,878,492 | 11/1989 | Sinofsky et al. . |
| 4,895,560 | 1/1990 | Papantonakos . |

(List continued on next page.)

OTHER PUBLICATIONS

E. Atherton & R. C. Sheppard; Solid Phase Peptide Synthesis a Practical Approach; Published by IRL Press 1989.
Donald A. Tomalia; Starburst™/Cascase Dendrimers: Fundamental Building Blocks for a New Nanoscopic Chemistry Set; Aldrichimica Acta, vol. 26, No. 4, 1993.

(List continued on next page.)

Primary Examiner—C. Fred Rosenbaum
Assistant Examiner—Perry E. Van Over
Attorney, Agent, or Firm—Briggs and Morgan

[57] ABSTRACT

A catheter having a therapeutic agent chemically bonded to a substrate on its exterior surface using a linker which photolytically releases the agent upon exposure to light energy at an appropriate wavelength. The linker is attached to the substrate via a complementary chemical group, with the opposing end containing an aromatic ring with a nitro group in the ortho position relative to a methyl or ethyl group which is functionalized to accept a complementary bond to the therapeutic agent. The substrate may include materials such as glass, polyamide, polyester, polyolefin, polypropylene, polyurethane, or latex. The therapeutic agent may include peptides, proteins, steroids, carbohydrates, nucleotides, or other aliphatic or heterocyclic products, and may be bonded to a molecular lattice or meshwork to accommodate a high molecular concentration per unit area and the inclusion of ancillary compounds such as markers or secondary emitters.

24 Claims, 15 Drawing Sheets

U.S. PATENT DOCUMENTS

| | | |
|---|---|---|
| 4,940,055 | 7/1990 | Brown . |
| 4,957,481 | 9/1990 | Gatenby . |
| 4,976,690 | 12/1990 | Solar et al. . |
| 4,994,033 | 2/1991 | Shockey et al. . |
| 4,997,431 | 3/1991 | Isner et al. . |
| 5,002,531 | 3/1991 | Bonzel . |
| 5,009,659 | 4/1991 | Hamlin et al. . |
| 5,026,367 | 6/1991 | Leckrone et al. . |
| 5,032,666 | 7/1991 | Hu et al. . |
| 5,047,025 | 9/1991 | Taylor et al. . |
| 5,053,033 | 10/1991 | Clarke . |
| 5,057,106 | 10/1991 | Kasevich et al. . |
| 5,061,273 | 10/1991 | Yock . |
| 5,086,068 | 2/1992 | Raleigh et al. . |
| 5,087,256 | 2/1992 | Taylor et al. . |
| 5,092,841 | 3/1992 | Spears . |
| 5,100,429 | 3/1992 | Sinofsky et al. . |
| 5,102,402 | 4/1992 | Dror et al. . |
| 5,106,386 | 4/1992 | Isner et al. . |
| 5,109,859 | 5/1992 | Jenkins . |
| 5,120,322 | 6/1992 | Davis et al. . |
| 5,126,140 | 6/1992 | Ito et al. . |
| 5,156,594 | 10/1992 | Keith . |
| 5,163,898 | 11/1992 | Morcos et al. . |
| 5,171,217 | 12/1992 | March et al. . |
| 5,171,264 | 12/1992 | Merrill . |
| 5,199,951 | 4/1993 | Spears . |
| 5,207,670 | 5/1993 | Sinofsky . |
| 5,217,482 | 6/1993 | Keith . |
| 5,232,446 | 8/1993 | Arney . |
| 5,236,410 | 8/1993 | Granov et al. . |
| 5,263,992 | 11/1993 | Guire . |

OTHER PUBLICATIONS

Kurt Nilsson and Klaus Mosbach; Tresyl Chloride–Activated Supports for Enzyme Immobilization; Methods in Enzymology, vol. 135 1987.

Stephen R. Adams and Roger Y. Tsien; Controlling Cell Chemistry With Caged Compounds; Am. Rev. Physiol. 1993.

James A. McCray and David R. Trentham; Properties and Uses of Photoreactive Caged Compounds; Am. Rev. Biophys. Chem. 1989.

Gordon W. McLean; Ania M. Owsianka; John H. Subak–Sharpe and Howard S. Marsden; Generation of Anti–Peptide and Anti–Protein Sera Effect of Peptide Presentation on Immunogenicity; Journal of Immunological Methods, 137 (1991).

E. Molnar, A.a Baude, S. A. Richmond, P. B. Patel, P. Somogyi, R. A. J. McIlhinney; Biocyhemical and Immunocytochemical Characterization of Antipeptide Antibodies to a Cloned GiuR1 Glutamate Receptor Subunit: Cellular and Subcellular Distribution in the Rat Forebrain; Neuroscience, vol. 53, No. 2, pp. 307–326, 1993.

Communication to the Editor; Photosensitive Protecting Groups; Journal of the American Chemical Society, 92:21, Oct. 21, 1970.

V. N. Rajasekharan PILLAI; Photoremnovable Protecting Groups in Organic Synthesis; 1980 George Thieme Publishers.

M. S. Sheu; A. S. Hoffman; J. Feijen; A Glow Discharge Treatment to Immobilize Poly(ethytlene oxide)/Poly(propylene oxide) surfactants for Wettable and Non–Fouling Biomaterials; J. Adhesion Sci. Technol., vol. 6, No. 9, pp. 905–1009 (1992).

David N. Posnett; Helen McGrath; James P. Tam; A Novel Method for Producing Anti–Peptide Antibodies; The Journal of Biological Chemistry; Feb. 5, 1988.

Victor S. Goldmacher; Peter D. Senter, John M. Lambert; Walter A. Blattler; Photoactivation of Toxin Conjugates; Bioconjugate Chem., vol. 3, No. 2, 1992.

R. B. Merrifield; Solid Phase Peptide Synthesis. I. The Synthesis of a Tetrapeptide; Jul. 20, 1963.

Obed W. Odom; Hung–Yin Deng; Alap R. Subramanian; Boyd Hardesty; Relaxation Time Interthiol Distance, and Mechanism of Action of Ribosomal Protein S1; Archives of Biochemistry and Biophysics; vol. 230, No. 1, pp. 178–193, Apr., 1984.

James P. Tam; Synthetic Peptide Vaccine Design; Synthesis and Properties of a High–Density Multiple Antigenic Peptide System; Proc. Natl. Acad. Sci. USA, vol. 85, pp. 5409–5413, Aug., 1988.

Protein Modification, Section E: ImmunoTechnology Catalog & Handbook; Published by Pierce.

H. Yasuda; Plasma Polymerization; Academic Press, 1985.

R. S. Schwartz, J. G. Murphy; W. D. Edwards; D. R. Holmes; Bioabsorbable, Drug–Eluting, Intracoronary Stents: Design and Future Applications; Coronary Stents, pp. 135–153, 1992.

D. J. Inman; W. E. Hornby; The Immobilization of Enzymes on Nylon Structures and Their Use in Automated Analysis; Biochem. J. 129, pp. 255–262, 1972.

N. J. Daka; K. J. Laidler; Flow Kinetics of Lactate Dehydrogenase Chemically Attached to Nylon Tubing; Can J. Biochem. vol. 56, 1978.

Communications to the Editor; Chemically Modified Polyesters as Supports for Enzyme Immobilization: Isocyanide, Acylhydrazide, and Aminoaryl Derivatives of Poly(ethylene Terephthalate); Biotechnology and Bioengineering, vol. XX, pp. 309–315 (1978).

T. T. Ngo; K. J. Laidler; C. F. Yam; Kinetics of Acetylcholinesterase Immobilized on Polyethylene Tubing; Can. J. Biochem., vol. 57, 1979.

Peter D. Senter; Marilyn J. Tansey; John M. Lambert; Walter A. Blaittler; Novel Photocleavable Protein Crosslinking Reagents and Their Use in the Preparation of Antibody–Toxin Conjugates; Photochemistry and Photobiology, vol. 42, No. 3, pp. 231–237, 1985.

Jeffery W. Walker; Gordon P. Reid; James A. McCray; David R. Trentham; Photolabile 1–(2 Nitrophenyl)ethyl Phosphate Esters of Adenine Nucleotide Analogues. Synthesis and Mechanism of Photolysis; J. Am Chem. Soc., vol. 110, No. 21, pp. 7170–7177 (1988).

Daniel H. Rich; S. K. Gurwara; Preparation of a New o–Nitrobenzyl Resin for Solid–Phase Synthesis of tert–Butyloxycarbonyl–Protected Peptide Acids; Journal of the American Chemical Society; 97:6; Mar. 19, 1975.

Ole Buchardt; Ulla Henriksen; Troels Koch; Peter E. Nielsen; Photolabeling Reagent Design; P. E. Nielsen (ed.), Photochemical Probes in Biochemistry, 1–9, 1989.

Nelson Carvajal; Jorge Martinez; Mireya Fernandez; Immobilised Monomers of Human Liver Arginase; Biochimica et Biophysica Acta, 481 (1977) 177–183.

John F. Wootton; David R. Trentham; 'Caged' Compounds to Probe the Dynamics of Cellular Processes: Synthesis and Properties of Some Novel Photosensitive P–2 Nitrobenzyl Esters of Nucleotides; P. E. Nielsen (ed.), Photochemical Probes in Biochemistry, 277–296 (1989).

William H. Scouten; A Survey of Enzyme Coupling Techniques; Methods in Enzymology, vol. 135 (1987).

von Thomas Doppler; Hans Schmidt; Hans–Jurgen; 32. Zur

Photochemie von 2, 1–Benzisoxazolen (Anthranilen) und Thermischen und Photochemischen Umsetzungen von 2–Axido–Acylbenzolen in Stark Saurer Losung; Helvetica Chimica Acta; vol. 62, Fasc. (1979) Nr. 32.

Michiko Iwamura; Touru Ishikawa; Yukiyoshi Koyama; Keisuke Sakuma; Hitzu Iwamura; 1–Pyrenylmethyl Esters, Photolabile Protecting Groups for Carboxylic Acids; Tetrahedron Letters, vol. 28, No. 6, pp. 679–682, 1987.

Surfaces in Biolaterials Foundation; Surface in Biolaterials '93 Symposium Notebook; Cambridge, Mass., Sep. 13–15, 1993.

Richard P. Haugland; Molecular Probes—Handbook of Fluorescent Probes and Research Chemicals; 5th Edition 1992–94; Molecular Probes, Inc.

The Cleveland Clinic Heart Center and The Center for Thrombosis and Vascular Biology; Restenosis Summit V Program; The Cleveland Clinic Foundation; May 20–21, 1993.

CATHETER SYSTEM FOR CONTROLLABLY RELEASING A THERAPEUTIC AGENT AT A REMOTE TISSUE SITE

BACKGROUND OF THE INVENTION

1. Field of the Invention

This invention relates generally to catheters capable of applying a chemical compound such as a drug or similar therapeutic agent to a remotely located tissue site through a restricted passage, and particularly to a low profile catheter system which utilizes light energy to selectively release that chemical compound.

2. Prior Art

Various catheters and related devices used to apply a drug or therapeutic compound to a specific tissue site are known to the art. Development of these systems has been most prevalent in the area of atherosclerosis treatment, particularly through percutaneous transluminal coronary angioplasty (PTCA) catheterization and related techniques.

Delivery of radiographic dyes and therapeutic compounds through the lumen and distal ports of angiography and angioplasty catheters has long been practiced. The technique has also been utilized in various thrombectomy, embolectomy, renal, esophageal, urethral, perfusion, and similar catheters both with and without dilation capabilities. U.S. Pat. No. 4,824,436 to Wolinsky is a representative example of a multiple-lumen dilation catheter designed to introduce heparin within a controlled region of the coronary vessel in order to inhibit smooth muscle cell hypertrophy or proliferation and therefore prevent restenosis. In addition to heparin, hirudin and its synthetic analogue fragment are often suggested to minimize hypertrophy, with antisense oligodeoxynucleotides also having been proposed. U.S. Pat. No. 4,994,033 to Shoekey similarly describes a system for releasing a liquid therapeutic agent directly through the dilation balloon of a coaxial over-the-wire PTCA catheter.

Dilation catheters having a coating which releases the therapeutic agent are also known. One representative example is U.S. Pat. No. 5,102,402 to Dror in which a microencapsulated compound is released upon expansion of the dilation balloon into contact with the surrounding tissue. Release is accomplished either by rupturing the microspheres upon contact with the arterial wall, or transfer of the microspheres to the arterial wall accompanied by subsequent degradation. Deformable porous microspheres could similarly be utilized in some applications, and U.S. Pat. No. 5,171,217 to March describes the delivery of several specific compounds through direct injection of microcapsules or microparticles using catheters of the type shown in Wolinsky '436.

U.S. Pat. No. 5,120,322 to Davis describes the process of coating the surface layer of a stent or shunt with a lathyrogenic agent to inhibit scar formation in the surrounding tissue during healing, thereby providing extended exposure to the therapeutic agent without requiring microencapsulation.

The use of electromagnetic energy—particularly in the form of microwave, radio frequency (rf), and coherent (laser) ultraviolet (uv) and visible-spectrum light energy within designated regions of the spectrum—has been adapted to angioplasty and atherectomy devices to accomplish a broad range of results.

U.S. Pat. No. 5,057,106 to Kasevich discloses the use of microwave energy for heating atherosclerotic plaque in the arterial wall in combination with dilation angioplasty. U.S. Pat. Nos. 4,807,620 to Strul and 5,087,256 to Taylor provide representative examples of atherectomy or angioplasty devices which convert electromagnetic rf energy to thermal energy. U.S. Pat. No. 5,053,033 to Clarke describes the use of an uv laser to inhibit restenosis by irradiation of smooth muscle cells with non-ablative cytotoxic light energy. U.S. Pat. Nos. 4,997,431 and 5,106,386 to Isner; 5,026,367 to Leckrone; 5,109,859 to Jenkins; and 4,846,171 to Kauphusman each disclose the use of laser light transmitted via an optical fiber or conduit to reduce tissue mass or remove arterial plaque by ablation. U.S. Pat. Nos. 4,878,492 to Sinofsky and 4,779,479 to Spears describe the use of nonablative laser light energy of sufficient wattage to heat the arterial plaque during a conventional PTCA dilation procedure in order to fuse fragmented plaque and coagulate trapped blood.

U.S. Pat. No. 5,100,429 to Sinofsky describes the process of forming a shunt in situ by applying a collagen-based adhesive to one side of a biologically-compatible sheet material, rolling that sheet material into a tube, positioning that tube at the selected site, and then applying light energy to crosslink the adhesive in order to bond the overlapping portions of the tube. A photodegradable adhesive coating may be used to initially secure the sheet material in position at the distal tip of a dilation catheter, with a second exposure of light energy at a discrete wavelength being used to release the crosslinked tube from the catheter. Similarly, U.S. Pat. No. 5,207,670 to Sinofsky describes the application of this principle to photoreactive suturing.

U.S. Pat. Nos. 5,092,841 and 5,199,951 to Spears each describe applying a coating of bioprotective material such as macroaggregated albumin or platelets to the external surface of a PTCA catheter, and then melting that coating and bonding it under pressure to the atherosclerotic lesion using thermal energy produced by laser light.

The various methods for introducing, delivering, or applying a drug or therapeutic agent to a specific site such as an atherosclerotic (stenotic) lesion or region of arterial plaque as described above have been shown to be beneficial, but each has concomitant problems or drawbacks.

Systems which deliver liquid agents or compounds within coronary arteries usually require either blocking a segment of the vessel for a prolonged period beyond that necessitated by the angioplasty procedure—after which the remaining agent is carried away by the bloodstream—or the use of relatively high and potentially damaging pressures to penetrate the arterial wall or plaque layer.

Microencapsulated coatings on catheters and stents permit longer exposure of the tissue to a particular compound or therapeutic agent, but the gross volume of the agent that can be effectively applied is significantly reduced due to the presence and limitations of the microcapsules themselves. Conversely, the concentration of the therapeutic agent can be increased, however this may result in exceeding the established protocols for such therapeutic agents to the point where patient-specific dosimetry can be required.

Exposed coatings generally require some type of sheath or shield that is removed from the catheter prior to the coating being melted or released. The sheath and any connections required to physically manipulate the sheath greatly increase the profile of the catheter, and limit the variety of applications for which such systems can be used. Moreover, the binders or adhesives used to formulate these coatings can account for the majority of their volume, and significantly dilute the concentration of the therapeutic agent.

The thermal and light energy required to melt and bond coatings such as macroaggregated albumin, to reduce tissue mass by ablation, and to inhibit restenosis by cytotoxic irradiation may also present concerns for damage to the arterial wall. These may include cytotoxic or cytogenic effects to healthy cells within (or even beyond) the tunica interna and tunica media, coagulation and subsequent release of incidental untrapped blood that may produce (or exacerbate) thrombosis or embolism, and similar deleterious results.

BRIEF SUMMARY OF THE INVENTION

It is therefore one object of this invention to design an extremely low profile catheter system that includes an exposed coating of a therapeutic agent such as a drug or similar chemical compound that may be applied precisely to a remotely located tissue site.

It is a related object of this invention to design the above catheter system such that it utilizes light energy to selectively release that therapeutic agent, while minimizing the potential damage to surrounding tissue due to thermal energy and cytotoxic or cytogenic effects.

It is a distinct object of this invention to design the above catheter system such that a relatively large volumes of concentrated therapeutic agent may be delivered by the catheter without a carrier, and that such therapeutic agents need not be diluted by a carrier or protected by an exterior sheath.

It is another object of this invention to design the above catheter system such that the release mechanism for the therapeutic agent can exist and operate independently of any other adjunct functionality or capability of the catheter, and without limiting or adversely affecting the structural design and construction of the catheter.

Briefly described, the drug-delivery catheter system of this invention includes a catheter having an exterior surface which includes a substrate of one or more functional chemical groups to which the therapeutic agent is covalently attached using a photosensitive linker. In the described embodiments, one end of the linker is attached to the substrate via a complementary chemical group, while the opposing end contains an aromatic ring with a nitro group in the ortho position relative to a methyl or ethyl group which is functionalized to accept a complementary bond to the therapeutic agent. The therapeutic agent is photolytically released from the linker by application of light energy at an appropriate wavelength.

The exterior surface of the catheter preferably has a microporous surface and may be fabricated in any suitable shape, including a simple cylindrical or tubular catheter tip, a collapsed dilation balloon, or a fiber optic element. The substrate may be selected from any suitable synthetic or natural polymer such as polyamide, polyester, polyolefin (polypropylene or polyethylene), polyurethane, or latex, or may be a solid material such as glass or quartz.

The therapeutic agent may be selected from a wide variety of drug classes or chemical compounds such as peptides, proteins, steroids, carbohydrates, nucleotides or other aliphatic or heterocyclic natural or synthetic products. The therapeutic agent may be bonded in a stacked configuration using a molecular lattice or meshwork to increase the number of bonding sites for the therapeutic agent, thereby accommodating a very high surface density or molecular concentration per unit area.

The light energy is preferably generated by a laser having one or more discrete wavelengths tuned to the optimal activation energy of the particular photolytic chemical bonds. Intermediate linkages to dye filters may be utilized to screen out transmitted energy at unused or antagonistic wavelengths (particularly cytotoxic or cytogenic wavelengths), and secondary emitters may be utilized to optimize the light energy at the principle wavelength of the laser source or the geometry of the catheter system.

DESCRIPTION OF THE PREFERRED EMBODIMENTS

Figure 1A:
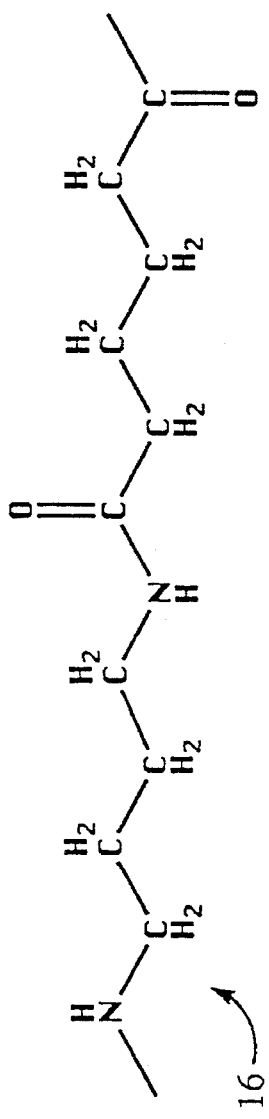
FIG. 1a is a diagram of a polyamide polymer (nylon 6) of the type that may be used to form the exterior surface and substrate layer for the drug-delivery catheter system of this invention.
Figure 1B:
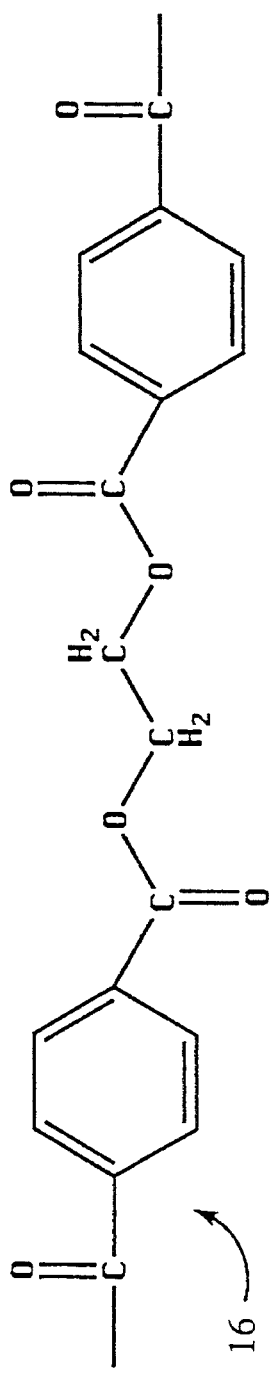
FIG. 1b is a diagram of a polyester polymer (PET, Dacron®) of the type that may be used to form the exterior surface and substrate layer for the drug-delivery catheter system of this invention.
Figure 1C:
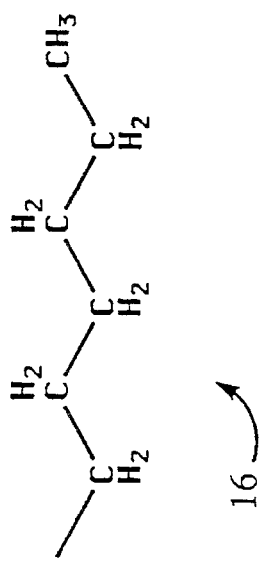
FIG. 1c is a diagram of a polyolefin polymer (polyethylene) of the type that may be used to form the exterior surface and substrate layer for the drug-delivery catheter system of this invention.
Figure 1D:
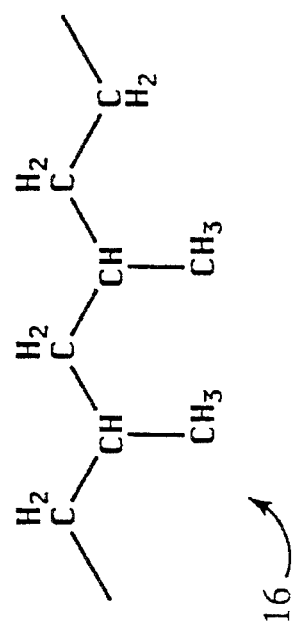
FIG. 1d is a diagram of a polyolefin polymer (polypropylene) of the type that may be used to form the exterior surface and substrate layer for the drug-delivery catheter system of this invention.
Figure 1E:
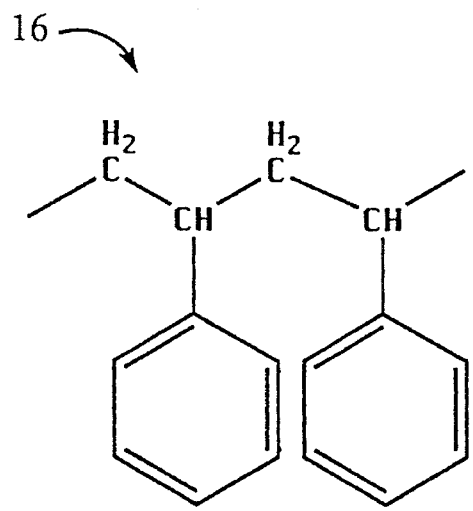
FIG. 1e is a diagram of a polystyrene polymer of the type that may be used to form the exterior surface and substrate layer for the drug-delivery catheter system of this invention.
Figure 1F:
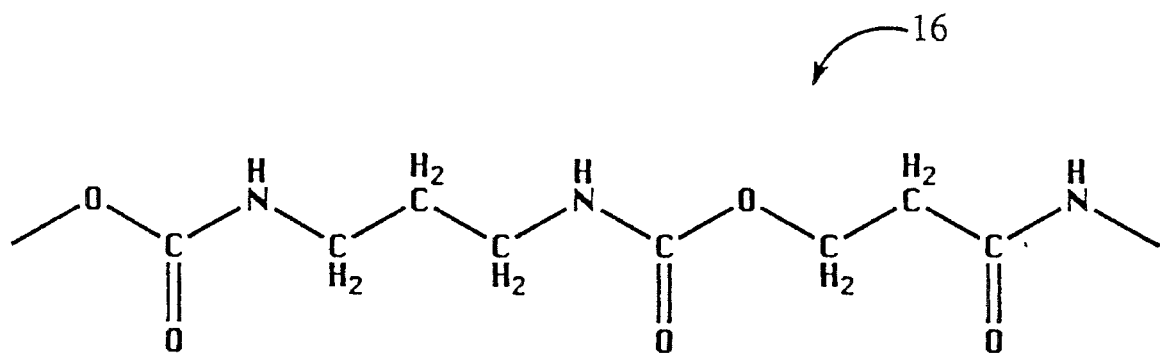
FIG. 1f is a diagram of a polyurethane polymer of the type that may be used to form the substrate layer for the drug-delivery catheter system of this invention.
Figure 1G:
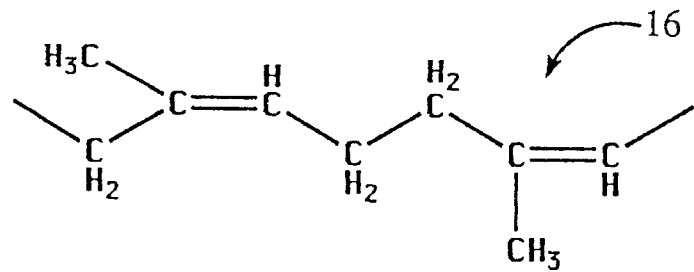
FIG. 1g is a diagram of a representative section of a latex polymer of the type that may be used to form the exterior surface and substrate layer for the drug-delivery catheter system of this invention.

The drug-delivery catheter system of this invention is shown in FIGS. 1–10 and referenced generally therein by the numeral 10. The various texts, articles, and patents discussed and cited within this specification and the corresponding documentation submitted herewith are hereby incorporated by reference as though fully and separately set forth herein.

In general, the drug-delivery catheter system 10 of this invention includes a catheter portion 12 or body defining an exterior surface 14 including a substrate layer 16 to which a photolabile or photolytic linker layer 18 is chemically bonded. Any one of several therapeutic agents 20 may be releasably connected to the substrate layer 16 on the catheter 10 by a complimentary chemical bond to the linker layer 18. In some applications, the substrate layer 16 may be only one or a few molecular layers on the exposed surface 14 of the catheter body 12, or alternately the substrate 16 may be built up to an extended depth or surface area using various techniques as described herein. The substrate 16 may also include various extenders 22 linking the surface 14 and substrate 16 to the linker layer 18 and therapeutic agent 20 as described in greater detail below, and the surface 14 and substrate 16 may be fabricated using a combination of Branched chain lattice and Polymer base (BPol) 24 as further described herein.

Figure 9:
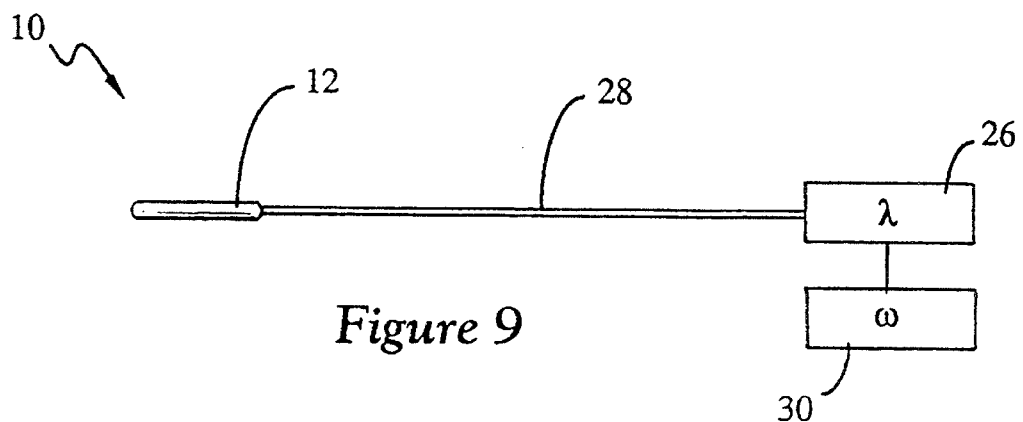
FIG. 9 is a diagrammatic view of the drug-delivery catheter system of this invention including a catheter, laser light source, and power supply.

Referring particularly to FIG. 9, the drug-delivery catheter system 10 includes the catheter portion 12, a source 26 of light energy (preferably coherent laser light of a predetermined wavelength), a fiber optic conduit 28 extending between and operatively connected to both the distal portion of the catheter body 12 and the source 26, and a power supply 30 for the source 26.

Figure 10:
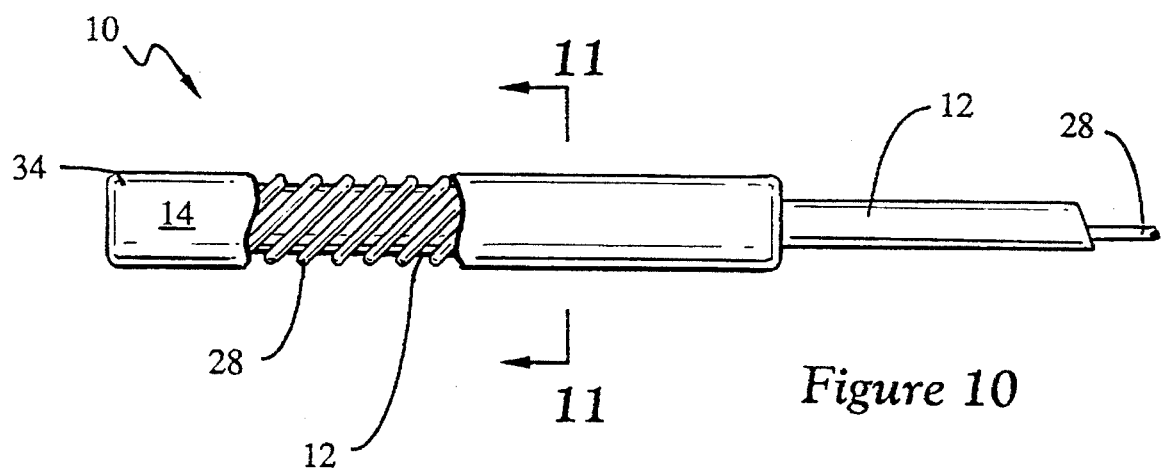
FIG. 10 is a partially broken away side elevation view of the distal catheter portion of the drug-delivery catheter system of FIG. 10.
Figure 11:
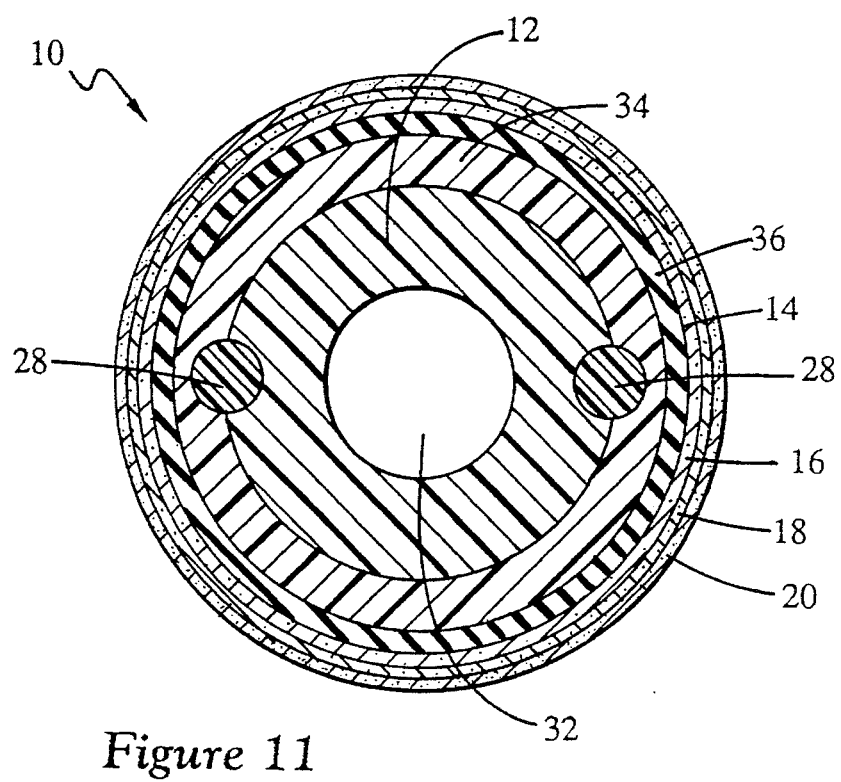
FIG. 11 is a cross section view of a balloon dilation angioplasty embodiment of the catheter portion of the drug-delivery catheter system of this invention taken through line 11–11 in FIG. 10.

Referring particularly to FIGS. 10 and 11, embodiments of the distal portion of the catheter body 12 are shown in which the fiber optic conduit 28 is disposed within and traverses the longitudinal portion of the catheter body 12 between the distal portion and the source 26, the fiber optic conduit 28 either being molded into the wall of the body 12 or received within a lumen 32. The fiber optic conduit 28 is then generally exposed in the region of the distal portion of the catheter body 12, and may utilize various geometries such as spiraling or circumscribing the catheter body 12 as shown in FIG. 10 and of which U.S. Pat. No. 4,878,492 to Sinofsky is a representative example. It may be readily appreciated that the particular geometry of the terminal end of the conduit 28 could include a straight ended conduit 28 of which U.S. Pat. No. 5,026,367 to Leckrone is a representative example, complex geometries such as shown in U.S. Pat. No. 5,109,859 to Jenkins, or simple projection structures such as shown in U.S. Pat. No. 5,053,033 to Clarke.

The catheter body 12 may include a covering 34 enclosing the conduit 28, that covering 34 defining the surface 14 as shown in FIG. 10 and being fabricated from a suitable polymer material as described herein to permit transmission of adequate light energy to accomplish the photolytic reaction and release the therapeutic agent 20.

Referring particularly to FIG. 11, a balloon dilation angioplasty embodiment of the distal portion of the drug-delivery catheter system 10 is shown in which the fiber optic conduit 28 is disposed partially within or between the catheter body 12 and covering 34, with a dilation balloon 36 surrounding the catheter body 12 and fluidly communicating with the lumen 32 such that the dilation balloon 36 may be selectively inflated or distended, and wherein the dilation balloon 36 therefore defines the surface 14 on which the substrate layer 16, linker layer 18, and therapeutic agent 20 are formed or applied.

The linker layer 18 in combination with the substrate layer 16 provides a photolytic release mechanism to selectively and responsively disconnect the therapeutic agent 20 from the substrate layer 16. One example described in detail below is the isomerization of 2 nitro benzyl compounds induced by exposure to light energy at the appropriate wavelength. It is anticipated that in various applications other bifunctional photolytic linkers 18 may be utilized to form the connection between the therapeutic agent 20 and substrate layer 16, and other types of photolytically reactive molecules or complexes may also be employed.

Since the substrate layer 16 may be selected from conventional biomedical catheter materials such as synthetic or natural polymers including polyamide, polyester, polyolefin (polypropylene or polyethylene), polyurethane, or latex, as well as solid substrates 16 such as glass or quartz, it may be readily appreciated that the outer surface 14 of the catheter 10 may itself form the substrate layer 16 and the body 12 of the catheter 10 may therefore be a generally homogeneous material for some applications.

As used herein, the term catheter 10 includes any generally tubular medical device for insertion into canals, vessels, passageways, or body cavities, whether or not including a lumen for the injection or withdrawal of fluids or the retention of an open passageway. The catheter 10 may include non-tubular and non-cylindrical structures adapted for particular biomedical uses, including probes and the distal extremities of other biomedical devices and apparatuses.

The design, fabrication, construction, or assembly of conventional catheters 10 may be utilized to provide certain capabilities required by the procedure being performed and to accomplish adjunct functions unrelated to the delivery or application of the therapeutic agent 20 to the remotely located tissue site. Conventional catheter designs that may be adapted for the site-specific application or delivery of a therapeutic agent 20 according to the methods described herein include percutaneous transluminal angiography (PTA) catheters, percutaneous transluminal coronary angioplasty (PTCA) catheters, vascular and peripheral vascular catheters, thrombectomy catheters, embolectomy catheters, renal catheters, esophageal catheters, perfusion catheters, upper and lower gastrointestinal catheters, bile duct and pancreatic duct catheters, urethral catheters, ureteral catheters, urogenital catheters, and similar catheters both with and without dilation capabilities. Central nervous system probes for diagnostic, therapeutic, and interventional uses, and probes or sensors designed for cellular modification that can be directed into a tissue site or even a cell via catheterization or direct exposure via an operative or in vitro technique are also subjects for the application or delivery of a therapeutic agent 20 according to the methods described herein.

The treatment of atherosclerosis—particularly through percutaneous transluminal coronary angioplasty (PTCA) catheterization and related techniques—appears to provide the most extensive immediate clinical use for this catheter system 10. However, the range of existing applications includes other medical procedures requiring remote application of drugs, such as in peripheral vascular disease, gastrointestinal disease, cancer, prostate and other urogenital applications, central nervous system intervention, and cellular modification both by situ or in vivo and by vitro (such as fertilization, stem cell manipulation, and other experimental clinical or laboratory procedures.) It is contemplated that this catheter system 10 may be adapted for use as an extremely low-profile fiber optic hypodermic system and it is anticipated that the methods may be adapted for devices used in veterinary or dental medicine as well as biological research including cell kinetics and physiology for intracellular research or cellular therapy.

The term therapeutic agent 20 does not imply any intended or required post-application activity or result, and may include virtually any synthetic or naturally occurring drug or chemical compound used for an accepted or experimental therapy, diagnostic application, or to accomplish an intended biomedical or biophysical purpose.

The therapeutic agent 20 may be selected from a wide variety of drug classes such as peptides, proteins, steroids, carbohydrates, nucleotides or other aliphatic or heterocyclic natural or synthetic products. Individual molecules of the therapeutic agent 20 may be bonded relative to the substrate layer 16 in a stacked configuration such that the longitudinal axes of the molecules of the therapeutic agent 20 are generally aligned with one another, and may approach being generally perpendicular to the surface 14 of the catheter body 12 and substrate 16, thereby accommodating a very high surface density or molecular concentration per unit area.

The process of fabricating a catheter 10 having a desired therapeutic agent 20 connected thereto and then controllably and selectively releasing that therapeutic agent 20 at a remote site within a patient may be summarized in five steps.

1. Formation of Substrate. The substrate layer 16 is formed on or applied to the surface 14 of the catheter body 12, and subsequently or simultaneously prepared for coupling to the linker layer 18. This is accomplished by modifying the substrate layer 16 to expose or add groups such as carboxyls, amines, hydroxyls, or sulfhydryls. In some cases, this may be followed by customizing the substrate layer 16 with an extender 22 that will change the functionality, for example by adding a maleimide group that will accept a Michael's addition of a sulfhydryl at one end of a bifunctional photolytic linker 18. The extent of this derivitization is measured by adding group-specific probes (such as 1 pyrenyl diazomethane for carboxyls, 1 pyrene butyl hydrazine for amines, or Edman's reagent for sulfhydryls Molecular Probes, Inc. of Eugene, Oregon or Pierce Chemical of Rockford, Ill.) or other fluorescent dyes that may be measured optically or by flow cytometry. The substrate layer 16 can be built up to increase its capacity by several methods, examples of which are discussed below.

2. Selection of Photolytic Release Mechanism. A heterobifunctional photolytic linker 18 suitable for the selected therapeutic agent 20 and designed to couple readily to the functionality of the substrate layer 16 is prepared, and may be connected to the substrate layer 16. Alternately, the photolinker 18 may first be bonded to the therapeutic agent 20, with the combined complex of the therapeutic agent 20 and photolytic linker 18 together being connected to the substrate layer 16.

3. Selection of the Therapeutic Agent. Selection of the appropriate therapeutic agent 20 for a particular clinical application will depend upon the prevailing medical practice. One representative example described below for current use in PTCA and PTA procedures involves the amine terminal end of a twelve amino acid peptide analogue of hirudin being coupled to a chloro carbonyl group on the photolytic linker 18. Another representative example is provided below where the therapeutic agent 20 is a nucleotide such as an antisense oligodeoxynucleotide where a terminal phosphate is bonded by means of a diazoethane located on the photolytic linker 18. A third representative example involves the platelet inhibitor dipyridamole (persantin) that is attached through an alkyl hydroxyl by means of a diazo ethane on the photolytic linker 18.

4. Fabrication of the Linker-Agent Complex and Attachment to the Substrate. The photolytic linker 18 or the photolytic linker 18 with the therapeutic agent 20 attached are connected to the substrate layer 16 to complete the catheter 10. A representative example is a photolytic linker 18 having a sulfhydryl disposed on the non-photolytic end for attachment to the substrate layer 16, in which case the coupling will occur readily in a neutral buffer solution to a maleimide-modified substrate layer 16 on the catheter 10. Once the therapeutic agent 20 has been attached to the catheter 10, it is necessary that the catheter 10 be handled in a manner that prevents damage to the substrate layer 16, photolytic linker layer 18, and therapeutic agent 20, which may include subsequent sterilization, protection from ambient light, heat, moisture, and other environmental conditions that would adversely affect the operation or integrity of the drug-delivery catheter system 10 when used to accomplish a specific medical procedure on a patient.

5. Photolytic Release of the Therapeutic Agent at a Specific Remote Tissue Site. The catheter 10 is operatively coupled to (or may itself include) the source 26 of light energy (not shown) of the appropriate wavelength to activate the photolytic linker 18, and exposure to that light energy selectively and controllably releases the therapeutic agent 20 from the substrate layer 16. The catheter 10 may be connected to the source 26 either before or after the catheter 10 is implanted or introduced into the patient, depending upon the particular type of catheter 10 being used and the nature of the medical procedure being undertaken. It may be appreciated that depending upon the construction of the bonds between the substrate layer 16, photolytic linker layer 18, and therapeutic agent 20, when the therapeutic agent 20 is released from the substrate 16 all or a portion of the photolytic linker 18 may remain connected to either the therapeutic agent 20 or the substrate layer 16.

The use of a coherent laser light source 26 will be preferable in many applications because the use of one or more discrete wavelengths of light energy that can be tuned or adjusted to the particular photolytic reaction occurring in the photolytic linker 18 will necessitate only the minimum power (wattage) level necessary to accomplish a desired release of the therapeutic agent 20. As discussed above, coherent or laser light sources 26 are currently used in a variety of medical procedures including diagnostic and interventional treatment, and the wide availability of laser sources 26 and the potential for redundant use of the same laser source 26 in photolytic release of the therapeutic agent 20 as well as related procedures provides a significant advantage. In addition, multiple releases of different therapeutic agents 20 or multiple-step reactions can be accomplished using coherent light of different wavelengths, intermediate linkages to dye filters may be utilized to screen out or block transmission of light energy at unused or antagonistic wavelengths (particularly cytotoxic or cytogenic wavelengths), and secondary emitters may be utilized to optimize the light energy at the principle wavelength of the laser source 26.

In other applications, it may be suitable to use a light source 26 such as a flash lamp operatively connected to the portion of the body 12 of the catheter 10 on which the substrate 16, photolytic linker layer 18, and therapeutic agent 20 are disposed. One example would be a mercury flash lamp capable of producing long-wave ultra-violet (uv) radiation within or across the 300–400 nanometer wavelength spectrum.

When using either a coherent laser light source 26 or an alternate source 26 such as a flash lamp, it is generally preferred that the light energy be transmitted through at least a portion of the body 12 of the catheter 10 such that the light energy traverses a path through the substrate layer 16 to the photolytic linker layer 18 in order to maximize the proportion of light energy transmitted to the photolytic linker layer 18 and provide the greatest uniformity and reproducibility in the amount of light energy (photons) reaching the photolytic linker layer 18 from a specified direction and nature. Optimal uniformity and reproducibility in exposure of the photolytic linker layer 18 permits advanced techniques such as variable release of the therapeutic agent 20 dependent upon the controlled quantity of light energy incident on the substrate layer 16 and photolytic linker layer 18.

The art pertaining to the transmission of light energy through fiber optic conduits 28 or other suitable transmission or production means to the remote biophysical site is extensively developed. For a fiber optic device, the fiber optic conduit 28 material must be selected to accommodate the wavelengths needed to achieve release of the therapeutic agent 20 which will for almost all applications be within the range of 280–400 nanometers. Suitable fiber optic materials, connections, and light energy sources 26 may be selected from those currently available and utilized within the biomedical field. While fiber optic conduit 28 materials may be selected to optimize transmission of light energy at certain selected wavelengths for desired application, the construction of a catheter 10 including fiber optic conduit 28 materials capable of adequate transmission throughout the range of the range of 280–400 nanometers is preferred, since this catheter 10 would be usable with the full compliment of photolytic release mechanisms and therapeutic agents 10. Fabrication of the catheter 10 will therefore depend more upon considerations involving the biomedical application or procedure by which the catheter 10 will be introduced or implanted in the patient, and any adjunct capabilities which the catheter 10 must possess.

Modification of Polymers and Solid Supports to
Form the Substrate Layer

Most polymers including those discussed herein can be made of materials which have modifiable functional groups or can be treated to expose such groups.

Polyamide (nylon) can be modified by acid treatment to produce exposed amines and carboxyls. Polyethylene terephthalate (PET, Dacron®) is a polyester and can be chemically treated to expose hydroxyls and carboxyls. Polystyrene has an exposed phenyl group that can be derivitized.

Polyethylene and polypropylene (collectively referred to as polyolefins) have simple carbon backbones which can be derivitized by treatment with chromic and nitric acids to produce carboxyl functionality, photocoupling with suitably modified benzophenones, or by plasma grafting of selected monomers to produce the desired chemical functionality. For example, grafting of acrylic acid will produce a surface with a high concentration of carboxyl groups, whereas thiophene or 1,6 diaminocyclohexane will produce a surface containing sulfhydryls or amines, respectively. The surface functionality can be modified after grafting of a monomer by addition of other functional groups. For example, a carboxyl surface can be changed to an amine by coupling 1,6 diamino hexane, or to a sulfhydryl surface by coupling mercapto ethyl amine.

Acrylic acid can be polymerized onto latex, polypropylene, polysulfone, and polyethylene terephthalate (PET) surfaces by plasma treatment. When measured by toluidine blue dye binding, these surfaces show intense modification. On polypropylene microporous surfaces modified by acrylic acid, as much as 50 nanomoles of dye binding per cm$^2$ of external surface area can be found to represent carboxylated surface area. Protein can be linked to such surfaces using carbonyl diimidazole (CDI) in tetrahydrofuran as a coupling system, with a resultant concentration of one nanomole or more per cm$^2$ of external surface. For a 50,000 Dalton protein, this corresponds to 50 μg per cm$^2$, which is far above the concentration expected with simple plating on the surface. Such concentrations of a therapeutic agent 20 on the angioplasty (PTCA) balloon of a catheter 10, when released, would produce a high concentration of that therapeutic agent 20 at the site of an expanded coronary artery. However, plasma-modified surfaces are difficult to control and leave other oxygenated carbons that may cause undesired secondary reactions.

In the case of balloon dilation catheters 10, creating a catheter body 12 capable of supporting a substrate layer 16 with enhanced surface area can be done by several means known to the art including altering conditions during balloon spinning, doping with appropriate monomers, applying secondary coatings such as polyethylene oxide hydrogel, branched polylysines, or one of the various Starburst™ dendrimers offered by the Aldrich Chemical Company of Milwaukee, Wis.

The most likely materials for the substrate layer 16 in the case of a dilation balloon catheter 10 or similar apparatus are shown in FIGS. 1a–1g, including synthetic or natural polymers such as polyamide, polyester, polyolefin (polypropylene or polyethylene), polyurethane, and latex. For solid support catheter bodies 12, usable plastics might include acrylamides, methacrylates, urethanes, polyvinylchloride, polysulfone, or other materials such as glass or quartz, which are all for the most part derivitizable.

Referring to the polymers shown in FIGS. 1a–1g, polyamide (nylon) is treated with 3–5M hydrochloric acid to expose amines and carboxyl groups using conventional procedures developed for enzyme coupling to nylon tubing. A further description of this process may be obtained from Inman, D. J. and Hornby, W. E., *The Iramobilization of Enzymes on Nylon Structures and their Use in Automated Analysis,* Biochem. J. 129:255– 262 (1972) and Daka, N. J. and Laidler, *Flow kinetics of lactate dehydrogenase chemically attached to nylon tubing,* K. J., Can. J. Biochem. 56:774–779 (1978). This process will release primary amines and carboxyls. The primary amine group can be used directly, or succinimidyl 4 (p-maleimidophenyl) butyrate (SMBP) can be coupled to the amine function leaving free the maleimide to couple with a sulfhydryl on several of the photolytic linkers 18 described below and acting as an extender 22. If needed, the carboxyl released can also be converted to an amine by first protecting the amines with BOC groups and then coupling a diamine to the carboxyl by means of carbonyl diimidazole (CDI).

Polyester (Dacron®) can be functionalized using 0.01N NaOH in 10% ethanol to release hydroxyl and carboxyl groups in the manner described by Blassberger, D. et al, *Chemically Modified Polyesters as Supports for Enzyme Iramobilization: lsocyanide, Acylhydrazine, and Aminoaryl derivatives of Poly(ethylene Terephthalate),* Biotechnol. and Bioeng. 20:309–315 (1978). A diamine is added directly to the etched surface using CDI and then reacted with SMBP to yield the same maleimide reacting group to accept the photolytic linker 18.

Polystyrene can be modified many ways, however perhaps the most useful process is chloromethylation, as originally described by Merrifield, R. B., *Solid Phase Synthesis. I. The Synthesis of a Tetrapeptide,* J. Am. Chem Soc. 85:2149–2154 (1963), and later discussed by Atherton, E. and Sheppard, R. C., *Solid Phase Peptide Synthesis: A Practical Approach,* pp. 13–23, (IRL Press 1989). The chlorine can be modified to an amine by reaction with anhydrous ammonia.

Polyolefins (polypropylene or polyethylene) require different approaches because they contain primarily a carbon backbone offering no native functional groups. One suitable approach is to add carboxyls to the surface by oxidizing with chromic acid followed by nitric acid as described by Ngo, T. T. et al., *Kinetics of acetylcholinesterase immobilized on polyethylene tubing,* Can. J. Biochem. 57:1200–1203 (1979). These carboxyls are then converted to amines by reacting successively with thionyl chloride and ethylene diamine. The surface is then reacted with SMBP to produce a maleimide that will react with the sulfhydryl on the photolytic linker 18.

A more direct method is to react the polyolefin surfaces with benzophenone 4-maleimide as described by Odom, O. W. et al, *Relaxation Time, Interthiol Distance, and Mechanism of Action of Ribosomal Protein S1,* Arch. Biochem Biophys. 230:178–193 (1984), to produce the required group for the sulfhydryl addition to the photolytic linker 18. The benzophenone then links to the polyolefin through exposure to ultraviolet (uv) light.

Other methods to derivitize the polyolefin surface include the use of radio frequency glow discharge (RFGD)—also known as plasma discharge—in several different manners to produce an in-depth coating to provide functional groups as well as increasing the effective surface area. Polyethylene oxide (PEO) can be crosslinked to the surface, or polyethylene glycol (PEG) can also be used and the mesh varied by the size of the PEO or PEG. This is discussed more fully by Sheu, M. S., et al., *A glow discharge treatment to immobilize poly(ethylene oxide)/poly(propylene oxide) surfactants for wettable and non-fouling biomaterials,* J. Adhes. Sci. Tech., 6:995–1009 (1992) and Yasuda, H., *Plasma Polymerization,* (Academic Press, Inc. 1985). Exposed hydroxyls can be activated by tresylation, also known as trifluoroethyl sulfonyl chloride activation, in the manner described by Nielson, K. and Mosbach, K., *Tresyl Chloride-Activated Supports for Enzyme Immobilization (and related articles),* Meth. Enzym., 135:65–170 (1987). The function can be converted to amines by addition of ethylene diamine or other aliphatic diamines, and then the usual addition of SMBP will give the required maleimide. Another suitable method is to use RFGD to polymerize acrylic acid or other monomers on the surface of the polyolefin. This surface consisting of carboxyls and other carbonyls is derivitizable with CDI and a diamine to give an amine surface which then can react with SMBP.

Figure 2:
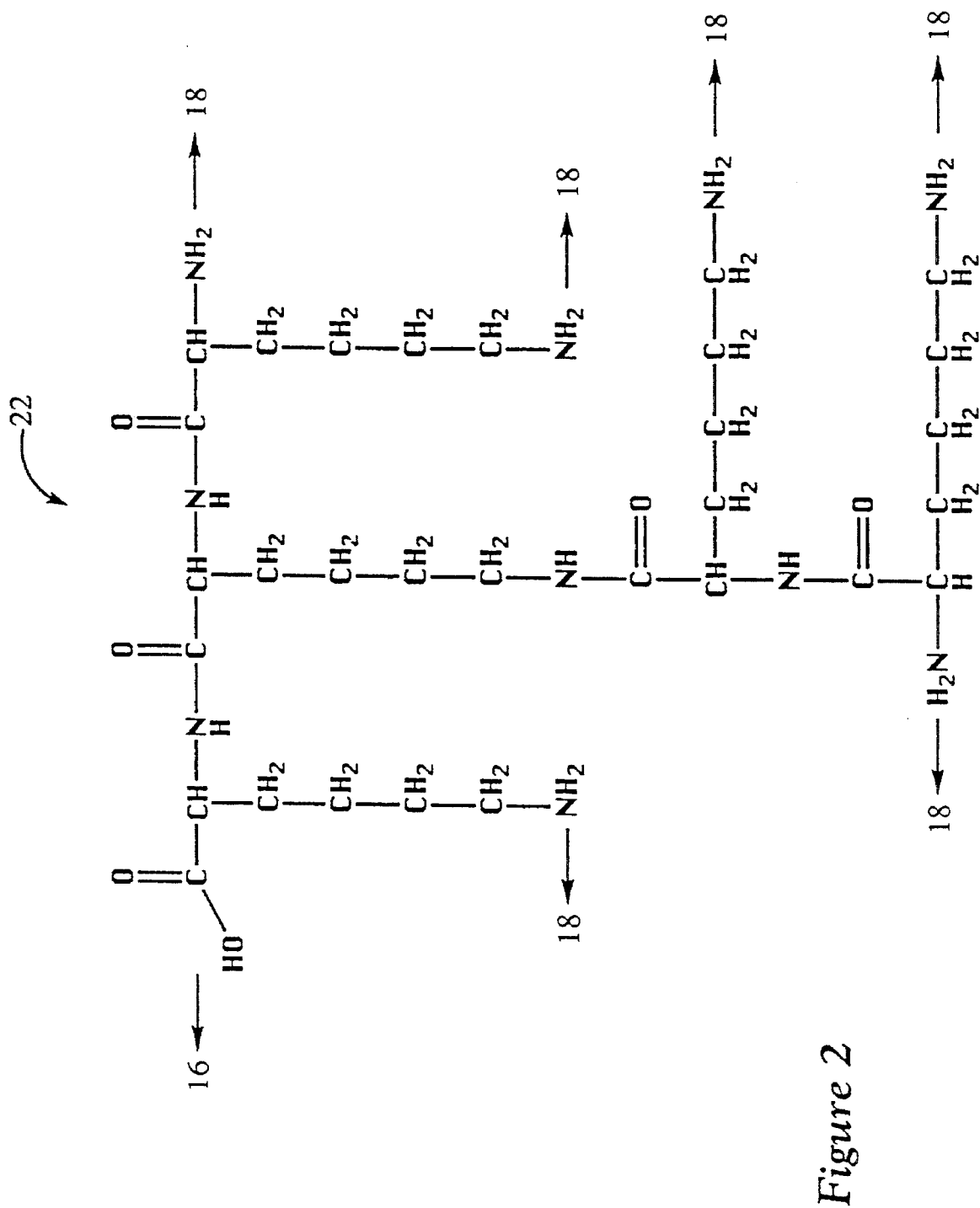
FIG. 2 is a diagram of a poly amino acid meshwork of the type that may be used to form an extender for the drug-delivery catheter system of this invention.

Increasing the effective surface area by amplifying the number of available binding sites can be accomplished by coupling a two-fold branching polylysine core or lattice to the surface as shown in FIG. 2, or by the use of Starburst™ dendrimers leaving amines available for subsequent addition of SMBP. The details of such techniques are described by Posnett, D. N. et al., *A Novel Method for Producing Antipeptide Antibodies,* J. Biol Chem., 263:1719–1725 (1988) and Tam, J. P., *Synthetic peptide vaccine design: Synthesis and properties of a high-density multiple antigenic system,* Proc. Nat. Acad. Sci. U.S.A. Vol. 85:5409–5413 (1988). An alternate strategy is to use polyethylene oxide star molecules of the type described in U.S. Pat. No. 5,171,264 to Merrill to form a branched polymer (BPol) complex 24 as the substrate 16 and surface 14, leaving hydroxyls which can be tresylated and converted to a maleimide as described above.

Referring particularly to FIG. 2, a complex extender 22 in the form of a loose lattice or meshwork can be created to increase or amplify the number of available binding sites per unit area, and to provide selective binding between molecules of the therapeutic agent 20 for spacers, dyes, markers, probes, or other ancillary agents. FIG. 2 shows a branched poly amino acid surface that achieves a six-fold amplification of available amines using a fluorenylmethoxycarbonyl-amino acid (Fmoc) peptide synthesis reaction to create a polylysine chain or meshwork that is built up in cycles as in conventional linear peptide synthesis, except that in alternate cycles the epsilon amine of lysine is protected by a different group that is removed from that cycle by a base while other epsilon amines remain protected. The next cycle results in a branched lysine, with the length of the intervening chain being controlled by varying the sequence of the differently protected epsilon amines. The polylysines are removed by triflouroacetic acid, which detaches the peptide and permits it to be coupled to the surface 14 of the catheter 12 through a carboxyl group released at the end of synthesis process. Alternately, the branched chain can be built up directly on the catheter 12 using a more stable first amino acid bond that is not be broken by the final deprotection cycle. Other variants are to alternate lysine with aspartic or glutamic acids to produce a bifunctional surface 14, to use cysteine for its sulfhydryl functionality, or to use intervening alanines as spacers without functionality. Variations on and applications of the Fmoc synthesis reaction, including several ancillary techniques, are discussed in detail by Atherton, E. and Sheppard, R. C., *Solid Phase Peptide Synthesis: A Practical Approach*, (IRL Press 1989).

Preparation of Photolytic Linkers and Linker-Agent Conjugates

Once a particular functionality for the substrate layer 16 has been determined, the appropriate strategy for coupling the photolytic linker 18 can be selected and employed. Several such strategies are set out in the examples which follow. As with selecting a method to expose a functional group on the surface 14 of the substrate layer 16, it is understood that selection of the appropriate strategy for coupling the photolytic linker 18 will depend upon various considerations including the chemical functionality of the substrate layer 16, the particular therapeutic agent 20 to be used, the chemical and physical factors affecting the rate and equilibrium of the particular photolytic release mechanism, the need to minimize any deleterious side-effects that might result (such as the production of antagonistic or harmful chemical biproducts, secondary chemical reactions with adjunct medical instruments including other portions of the catheter 10, unclean leaving groups or other impurities), and the solubility of the material used to fabricate the catheter body 12 or substrate layer 16 in various solvents.

More limited strategies are available for the coupling of a 2-nitrophenyl photolytic linker 18. If the active site is 1-ethyl hydrazine used in most caging applications, then the complementary functionality on the therapeutic agent 20 will be a carboxyl, hydroxyl, or phosphate available on many pharmaceutical drugs.

If a bromomethyl group is built into the photolytic linker 18, it can accept either a carboxyl or one of many other functional groups, or be converted to an amine which can then be further derivitized. In such a case, the leaving group might not be clean and care must be taken when adopting this strategy for a particular therapeutic agent 20.

Other strategies include building in an oxycarbonyl in the 1-ethyl position, which can form an urethane with an amine in the therapeutic agent 20. In this case, the photolytic process evolves $CO_2$.

EXAMPLE 1

Figure 3A:
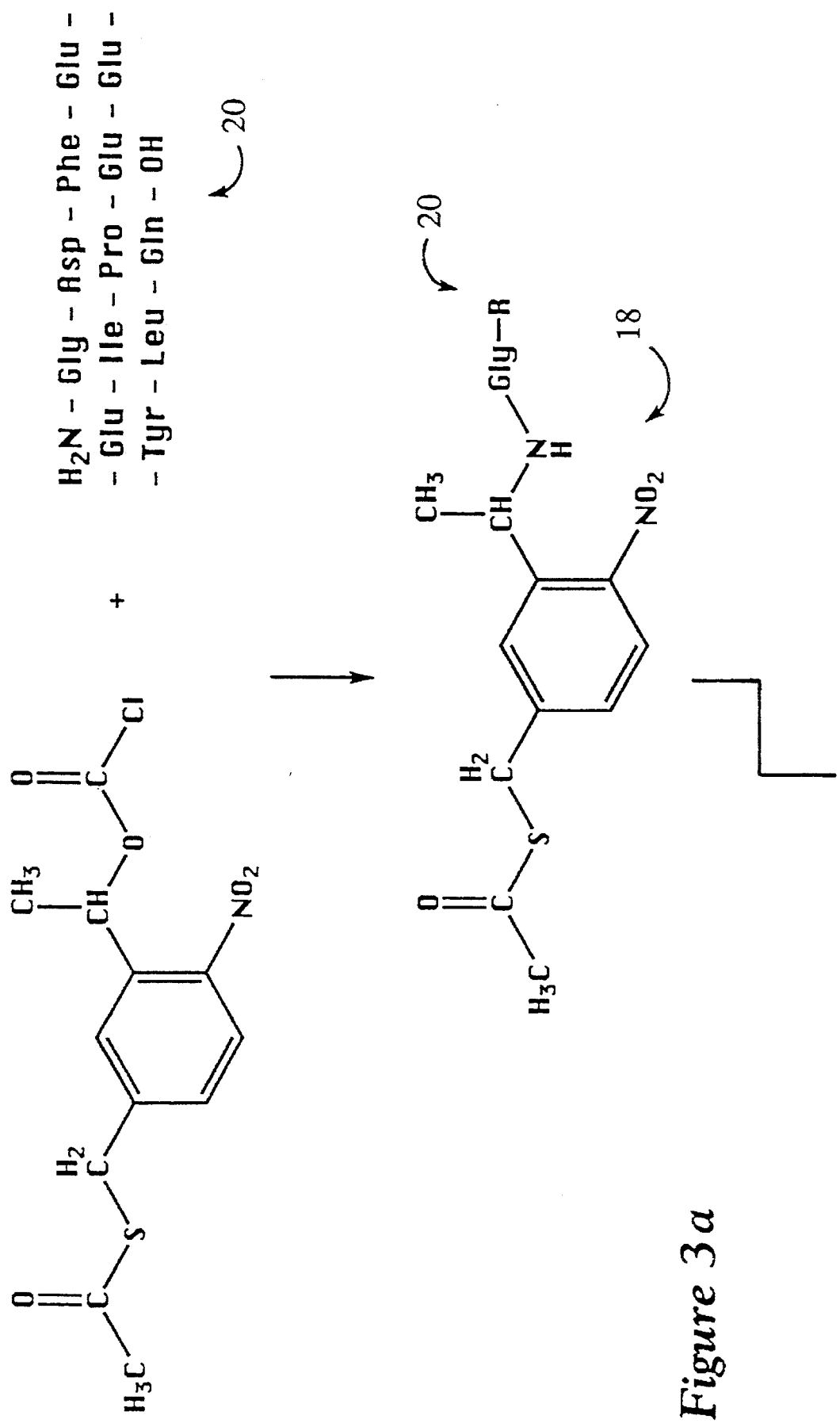
FIG. 3a is a diagram of the initial stage of the reaction pathway for forming a carbonyl chloride photolytic linkage to a peptide therapeutic agent for the drug-delivery catheter system of this invention.
Figure 3B:
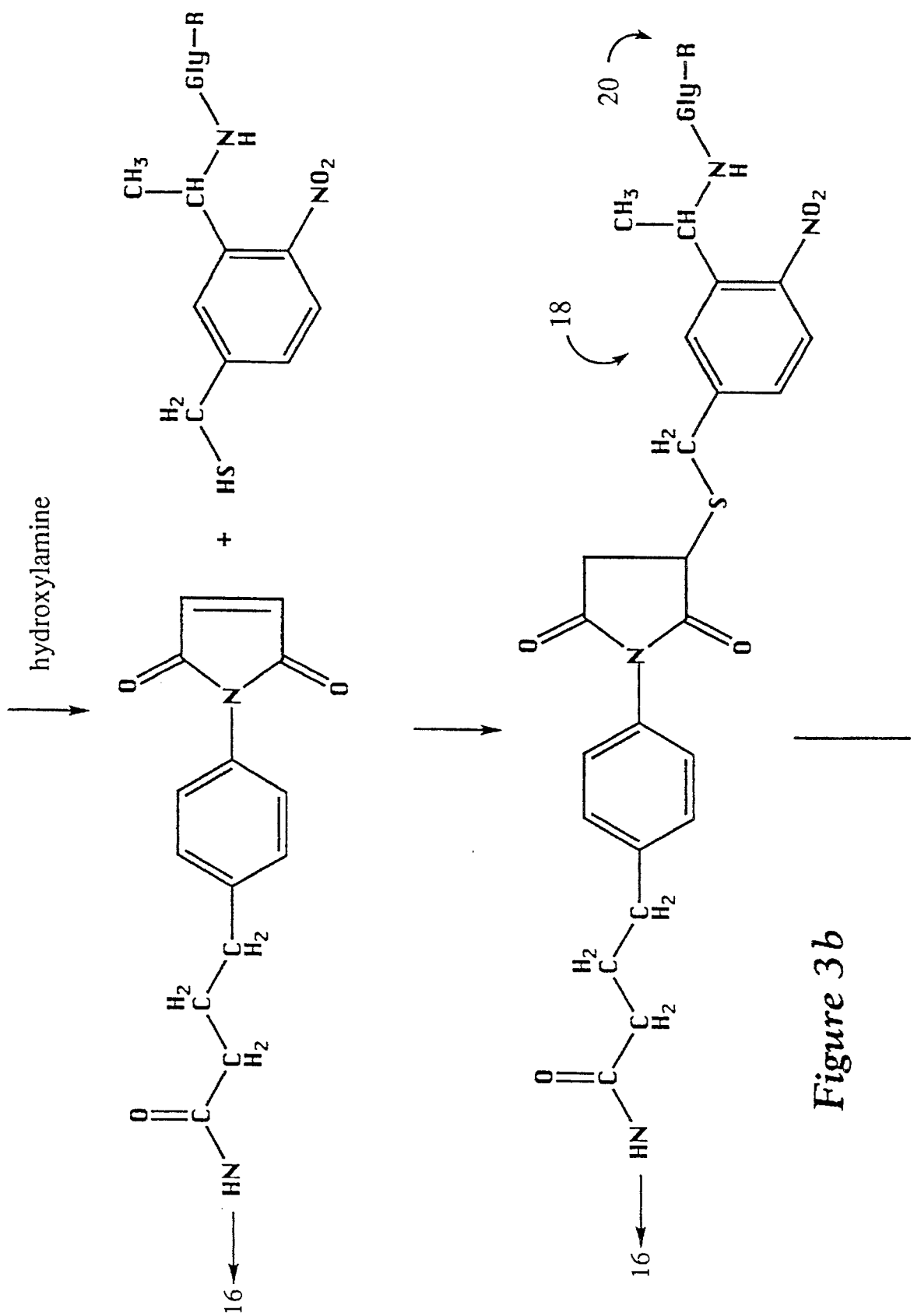
FIG. 3b is a diagram of the intermediate stage of the reaction pathway shown in FIG. 3a for forming a carbonyl chloride photolyric linkage to a peptide therapeutic agent for the drug delivery catheter system of this invention.
Figure 3C:
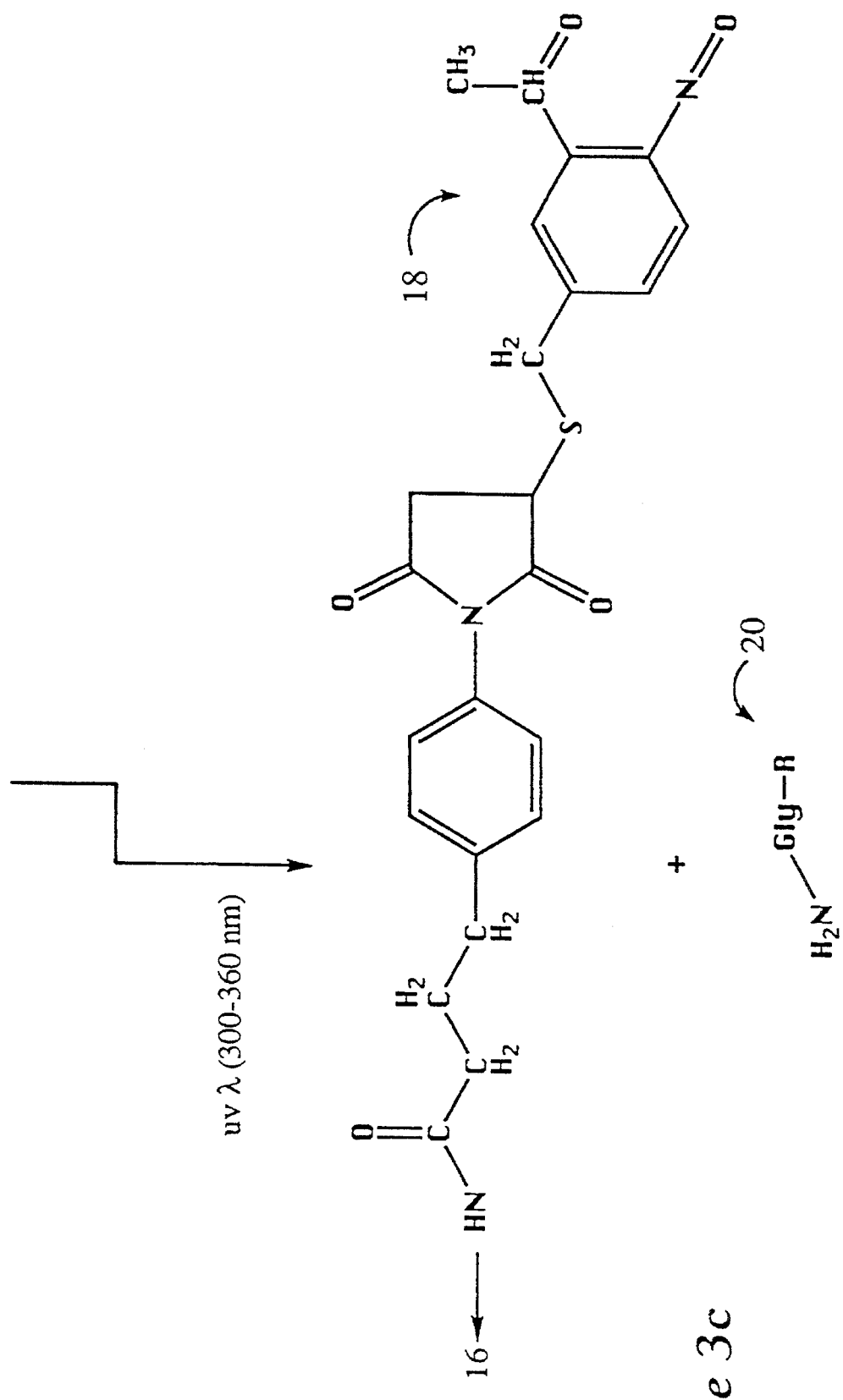
FIG. 3c is a diagram of the final stage of the reaction pathway shown in FIGS. 3a and 3b for forming a carbonyl chloride photolyric linkage to a peptide therapeutic agent for the drug delivery catheter system of this invention.

One representative example as shown in FIG. 3a–3c uses a carbonyl chloride linkage for the photolytic linker 18 and the peptide fragment hirudin (54–65) (SEQ. ID. NO:1) as the therapeutic agent 20 to create a catheter 10 that would deliver this peptide to a remote site such as a coronary artery and be selectively and controllably released using ultraviolet (uv) light in the range of 300–400 nanometers using a photolabile heterobifunctional crosslinking agent such as described by Senter, P. D., et al., *Novel Photoclearable Protein Crosslinking Reagents And Their Use In The Preparation Of Antibody Toxin Conjugates*, Photochem. and Photobiol. 42:231–237 (1985) and Goldmacher, V. S., et al., *Photoactivation of Toxin Conjugates*, Bioconjug. Chem. 3:104–107 (1992).

The structure of the peptide fragment hirudin (54–65) is $H_2N$-Gly-Asp-Phe-Glu -Glu-Ile-Pro-Glu-Glu-Tyr-Leu-Gln-OH. This peptide is unique with several appended carboxyls and only two primary amines. It can be coupled to the photolytic linker 18 either by means of the amines or one of the several carboxyls on the glutamic acid residues. In this example, coupling to the N-terminal primary amine (or possibly the glutamine amine) is described.

The compound (4 nitro-3 (1-carbonyl chloro ethyl) phenyl) methyl 3-S-acetothioic acid ester (Compound 1) is reacted with the peptide in 0.001 M $NaCO_3$ at ph 8.3. The conjugate is purified by gel filtration or HPLC and the thioester reduced to the free sulfhydryl by 0.5M hydroxylamine in 0.001M EDTA at Ph 7.3. The peptide-linker conjugate is then incubated with the catheter body 12 and surface 14 (for example, a polyamide angioplasty dilation balloon modified as described above with maleimide to produce the substrate layer 16) in a 0.1M potassium phosphate buffer containing 0.5M EDTA at pH 7.0 overnight. The catheter body 12 and surface 14 are then removed from the incubation media and washed several times in buffer. The concentration of therapeutic agent 20 on the surface 14 can be estimated by the difference between the starting solution and the remaining peptide 20 and linker 18 (or peptide-linker conjugate) in the washes from the coupling. The balloon is then dried and the surface protected for the subsequent steps in attaching the balloon to the remainder of a conventional introducer system for an angioplasty (PTCA) catheter 10. The balloon may then be used for angioplasty followed by photolytic release of the hirudin peptide fragment 20 upon exposure to ultraviolet (uv) light at a wavelength of approximately 300–360 nanometers.

EXAMPLE 2

This example provides a photolytic linker 18 with a 1-diazoethane group positioned ortho to the nitro that will react with a carboxyl, hydroxyl, or phosphate to form a photolytic release mechanism. The example uses the same principle adopted for molecular caging by forming a compound with a 1-diazoethane on a nitro benzyl compound.

Figure 4A:
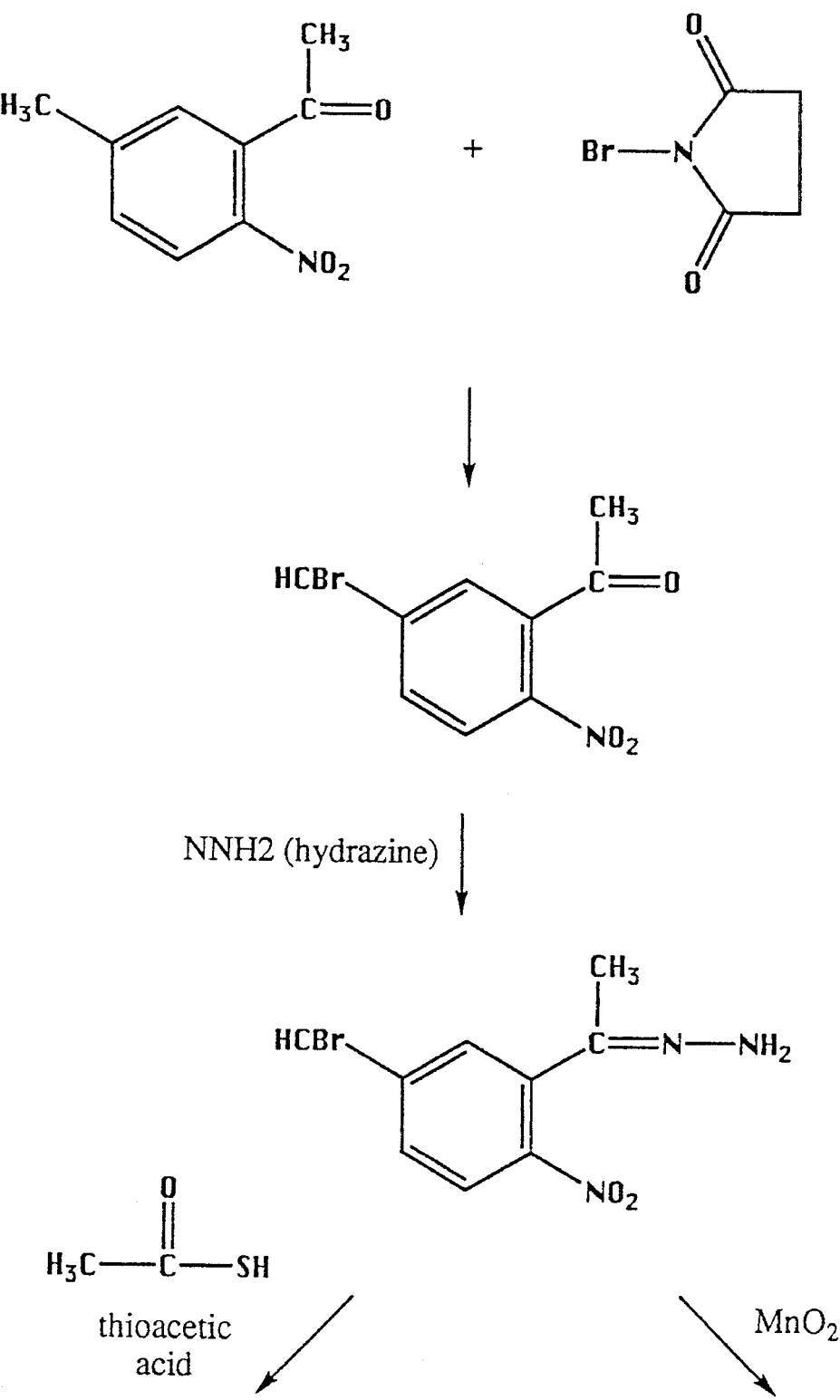
FIG. 4a is a diagram of the initial stage of the reaction pathway for forming a hydrazine photolytic linkage for the drug-delivery catheter system of this invention.
Figure 4B:
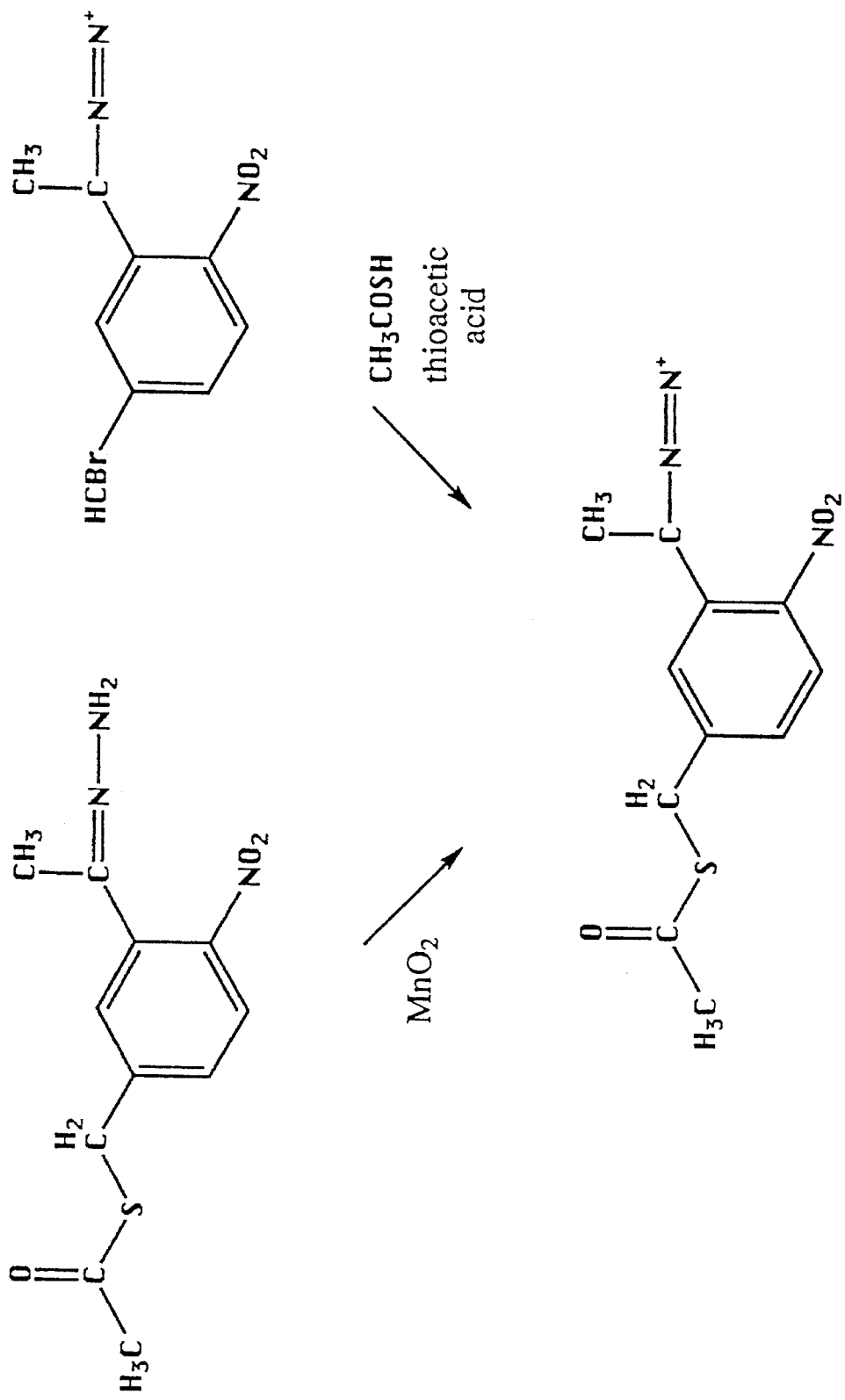
FIG. 4b is a diagram of the final stage of the reaction pathway shown in FIG. 4a for forming a hydrazine photolytic linkage for the drug delivery catheter system of this invention.
Figure 5A:
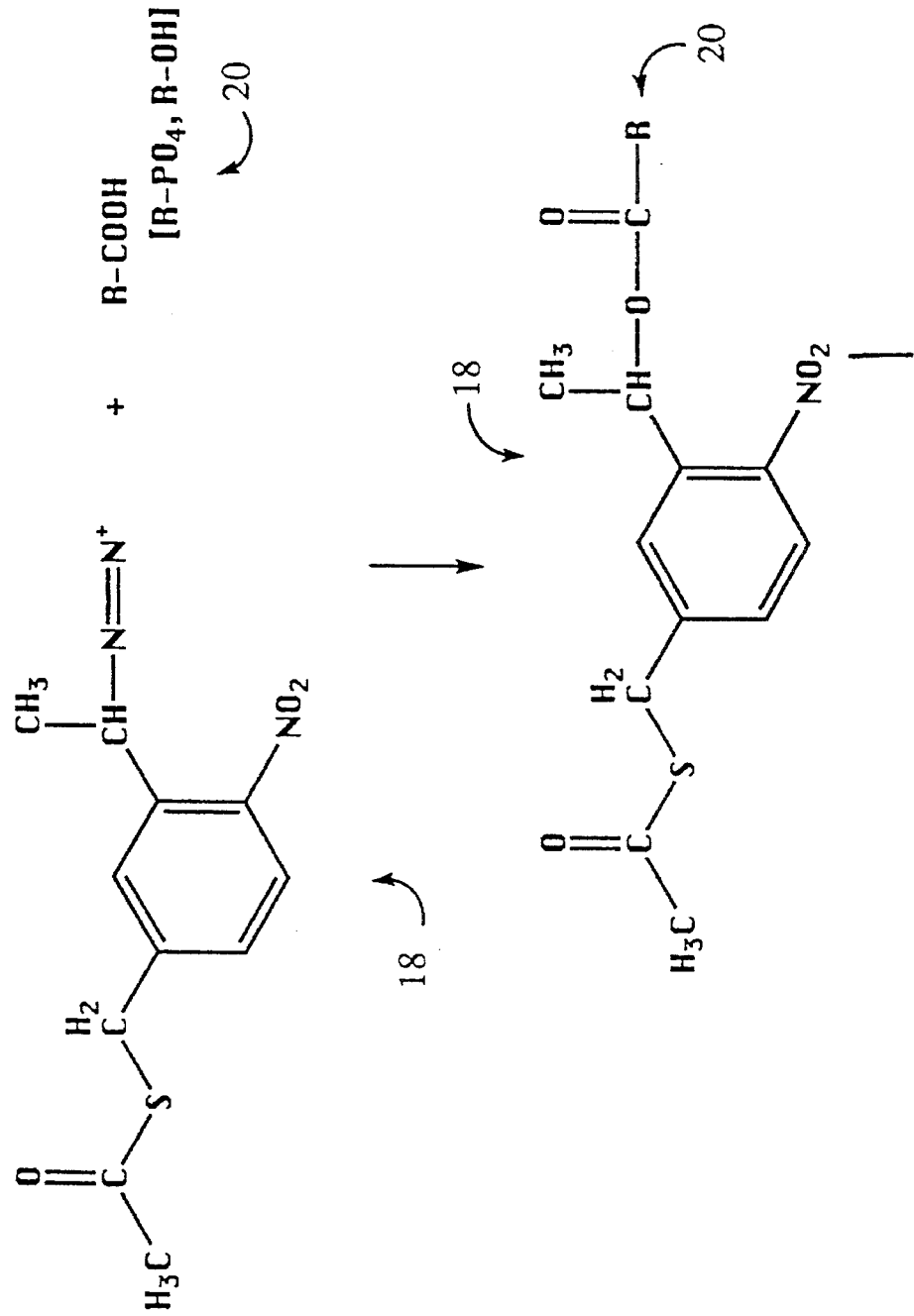
FIG. 5a is a diagram of the initial stage of the reaction pathway for forming a linkage to a carboxyl-, phosphate-, or hydroxyl-containing therapeutic agent for the drug-delivery catheter system of this invention.
Figure 5B:
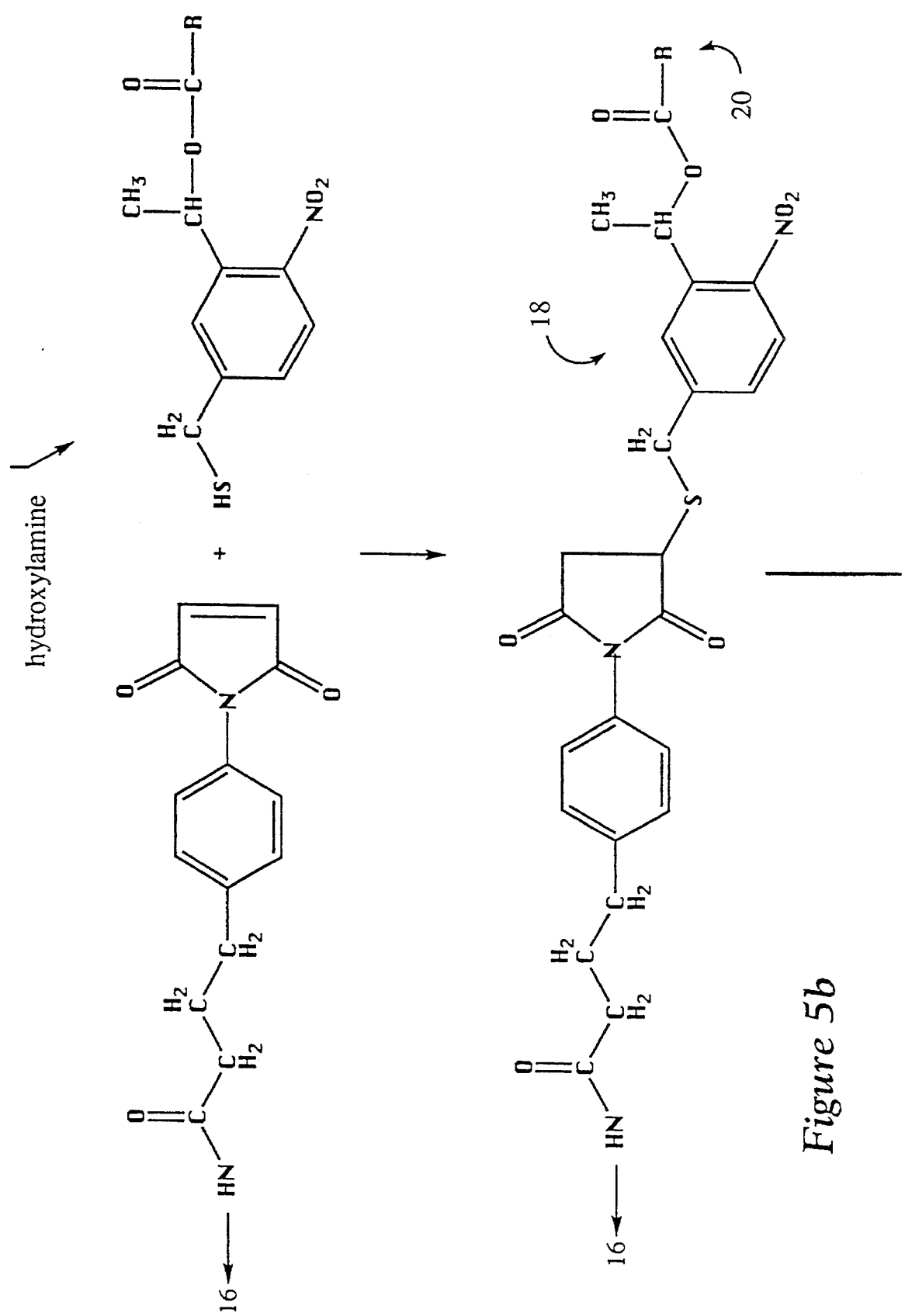
FIG. 5b is a diagram of the intermediate stage of the reaction pathway shown in FIG. 5a for forming a linkage to a carboxyl-, phosphate-, or hydroxyl-containing therapeutic agent for the drug-delivery catheter system of this invention.
Figure 5C:
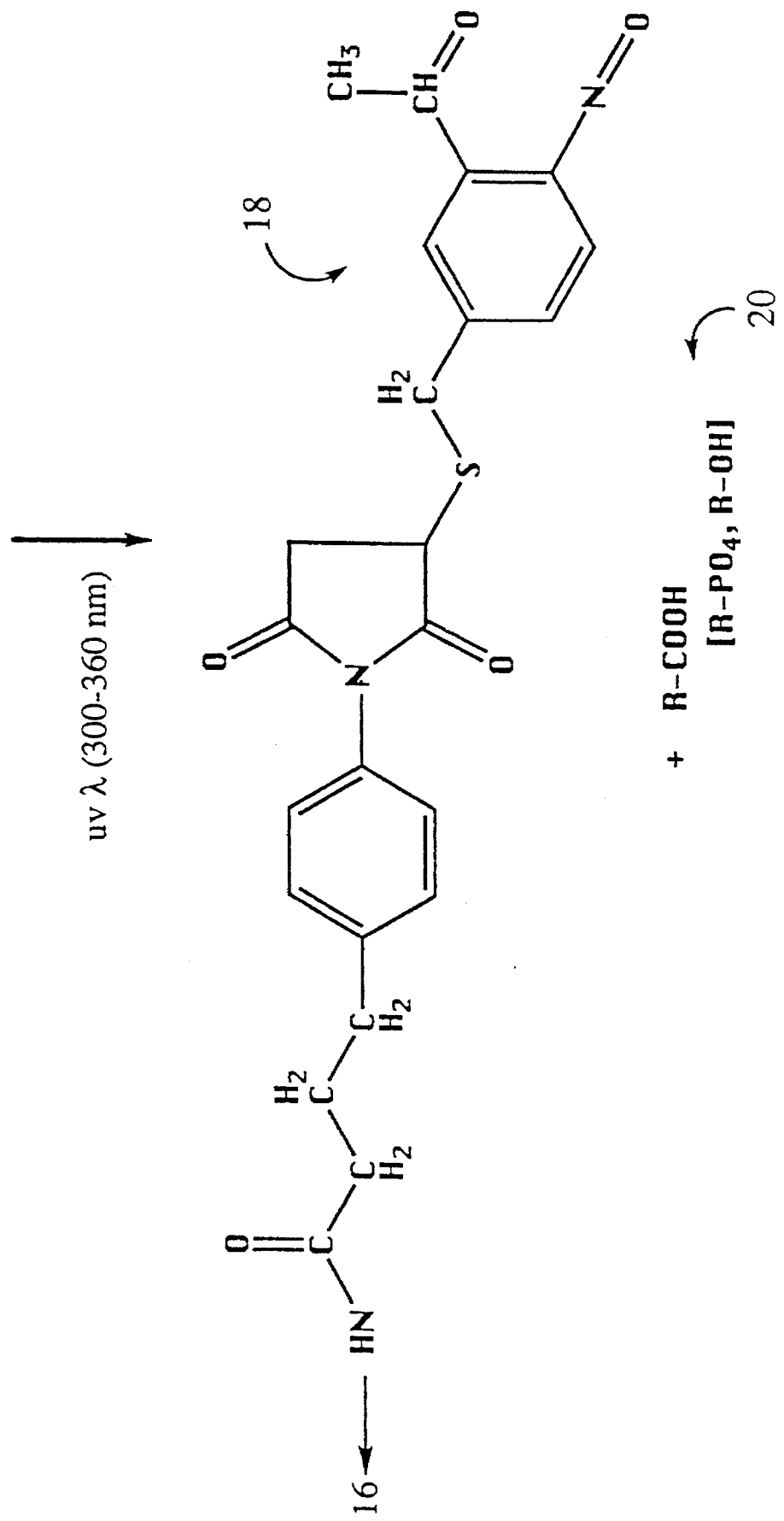
FIG. 5c is a diagram of the final stage of the reaction pathway shown in FIGS. 5a and 5b for forming a linkage to a carboxyl-, phosphate-, or hydroxyl-containing therapeutic agent for the drug-delivery catheter system of this invention.

Referring particularly to FIGS. 4a and 4b, the active group is a 1-diazoethane on the phenyl ring ortho to a nitrate group. FIGS. 4a and 4b display one of several schemes to produce a compound similar to Compound 1 described above in Example 1. In this example, the initial compound 1-(5 methyl-2-nitrophenyl) ethanone is similarly prepared as described by Senter, P. D., et al., *Novel Photoclearable Protebt Crosslinking Reagents And Their Use In The Preparation Of Antibody Toxin Conjugates,* Photochem. and Photobiol. 42:231–237 (1985), and Doppler, T. et al., *On the Photochemistry of 2,1-Benzisoxazoles (Anthraniles) ant on the Thermal and Photochemical Decomposition of 2 -Azidoacylbenzenes in Strongly Acidic Solution,* Helva. Chim. Acta 62:271–303 (1979). In this case, the ethanone is brominated at the 5-methyl position and the resulting compound is treated in 95% ethanol with hydrazine hydrate in glacial acetic acid to form the hydrazone, as discussed by Walker, J. W., et al., *Photolabile 1-(2-Nitrophenyl)ethyl Phosphate Esters of Adenine Nucleotide Analogues. Synthesis and Mechanism of Photolysis,* J. Am. Chem. Soc. 110:7170–7177 (1988). The hydrazone is then oxidized in trichloromethane with $MnO_2$ to form hydrazine, which is the desired group. This compound is then treated with thioacetic acid to form the thio ester, which is converted to a sulfhydryl with hydroxyl amine to give a free sulfhydryl. The carboxyl, phosphate, or hydroxyl group of a therapeutic agent 20 can be coupled to the hydrazine by a two-phase method as described by Walker, J. W. et al., *Photolabile 1-(2-Nitrophenyl)ethyl Phosphate Esters of Adenine Nucleotide Analogues. Synthesis and Mechanism of Photolysis,* J. Am. Chem. Soc. 110:7170–7177 (1988) and Wootten, J. F., et al., *'Caged' Compounds to Probe the Dynamics of Cellular Processes: Synthesis and properties of some Novel Photosensitive P- 2-Nitrobenzyl Esters of Nucleotides,* Photochemical Probes in Biochemistry, pp. 277–296 (1989).

The therapeutic agent 20-photolytic linker 18 complex can then be treated with the maleimide modified substrate layer 16 to complete the formation of the delivery complex.

To optimize this scheme, it may be necessary in some applications to change the order of the reaction steps to prevent interference. For example, it may be necessary in some instances to convert the 5-bromo methyl phenyl ethanone compound directly to the sulfhydryl, and then attach this to the maleimide treated substrate layer 16 prior to converting the ethanone to the hydrazone and subsequently to the diazo compound. An alternate process would entail proceeding first to the hydrazone, then preparing the sulfhydryl, coupling to the substrate layer 16, oxidizing the hydrazone, and finally adding the therapeutic agent 20. It should be noted that the diazo compound is unstable and needs to be coupled directly to the therapeutic agent 20.

Figure 6:
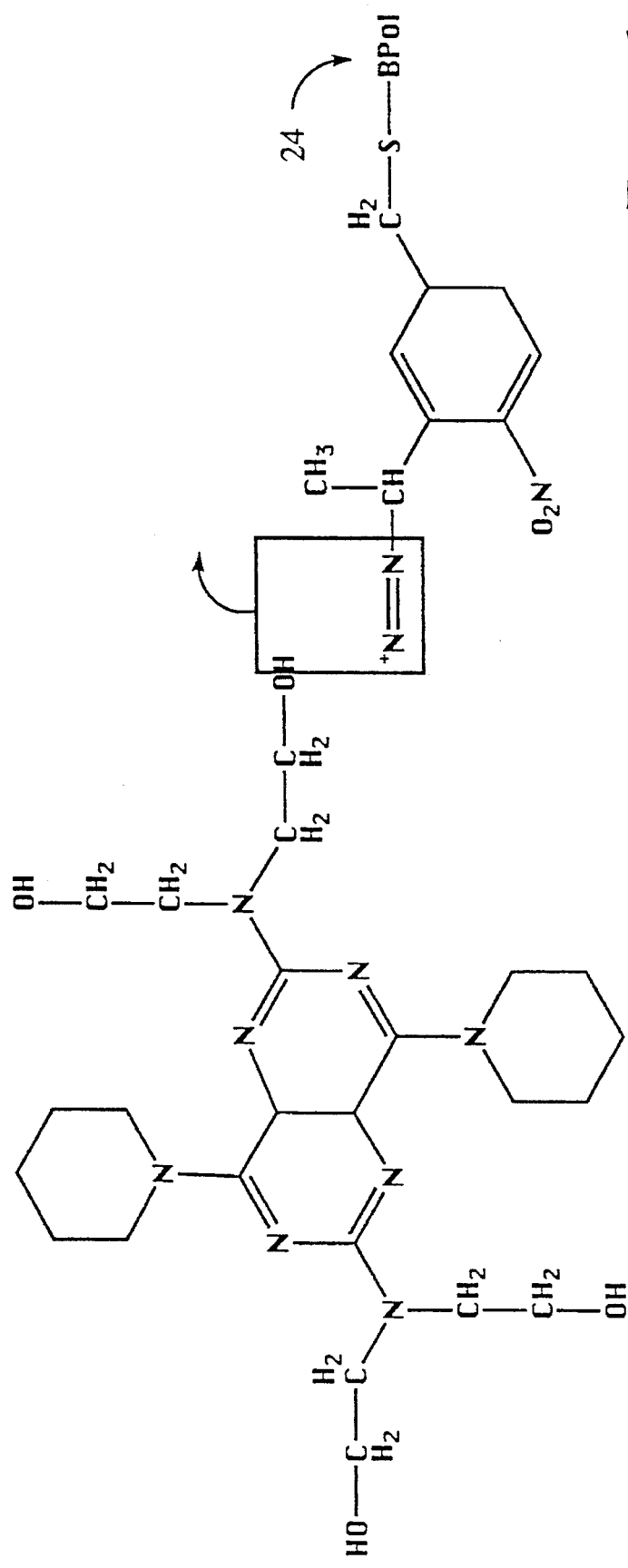
FIG. 6 is a diagram of a photolytic linkage between a branched chain-polymer complex (BPol) for the substrate layer and a dipyridamole (Persantin) therapeutic agent for the drug-delivery catheter system of this invention.
Figure 7:
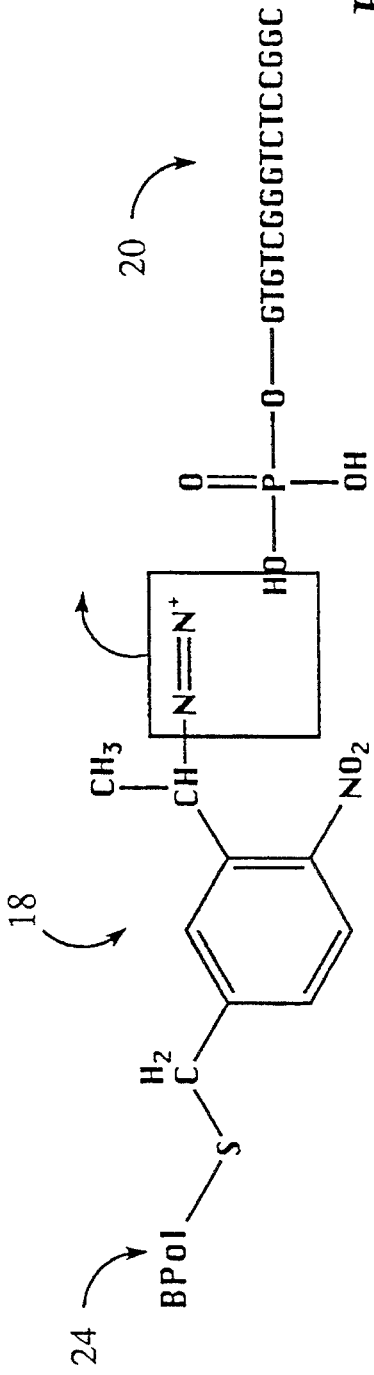
FIG. 7 is a diagram of a photolytic linkage between a branched chain-polymer complex (BPol) for the substrate layer and an antisense oligodeoxynucleotide (ODN) therapeutic agent for the drug-delivery catheter system of this invention, wherein G represents guanine, T represents thymidine, and C represents cytosine within the oligodeoxynucleotide.
Figure 8A:
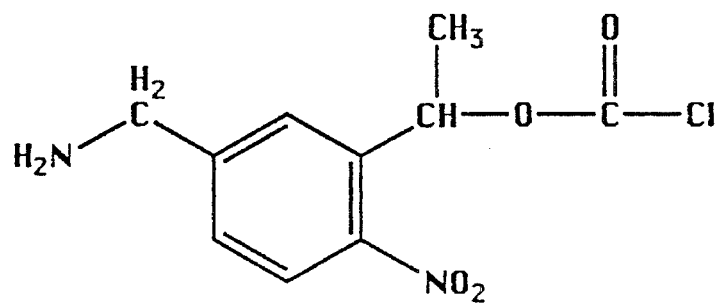
FIG. 8a is a diagram of a chloroformate precursor for an amine linkage for the drug-delivery catheter system of this invention.
Figure 8B:
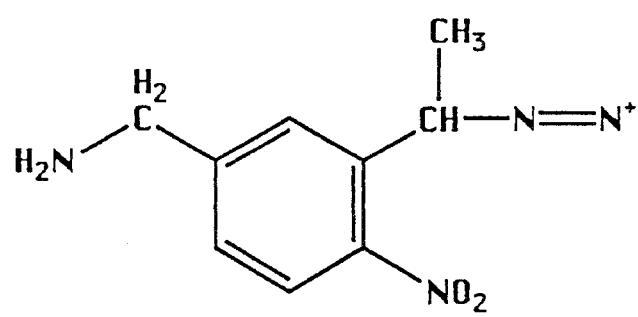
FIG. 8b is a diagram of a hydrazine precursor with an amine function for the drug-delivery catheter system of this invention.
Figure 8C:
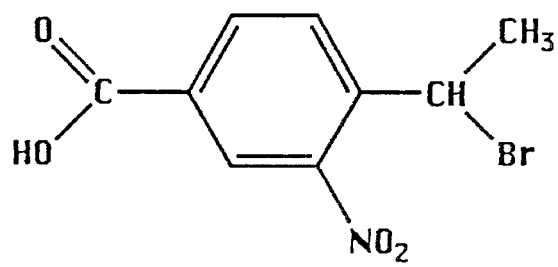
FIG. 8c is a diagram of a brominated precursor with a carboxyl function for the drug-delivery catheter system of this invention.
Figure 8D:
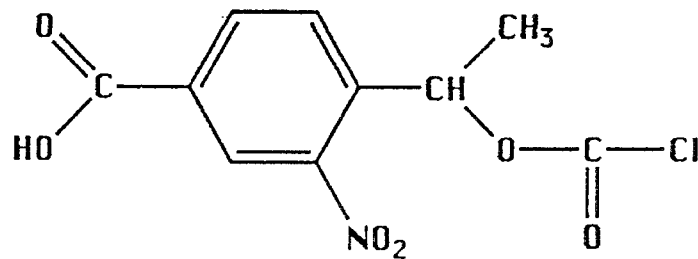
FIG. 8d is a diagram of a chloroformate precursor with a carboxyl function for an amine linkage for the drug-delivery catheter system of this invention.
Figure 8E:
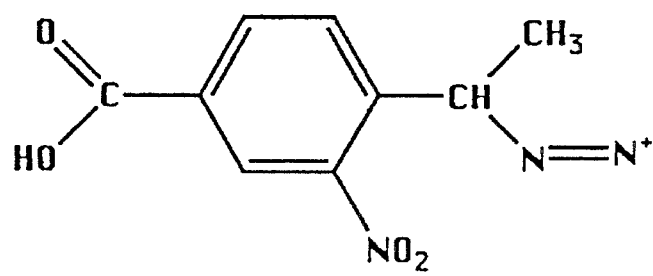
FIG. 8e is a diagram of a representative example of a hydrazine precursor with a carboxyl function for the drug-delivery catheter system of this invention.
Figure 8F:
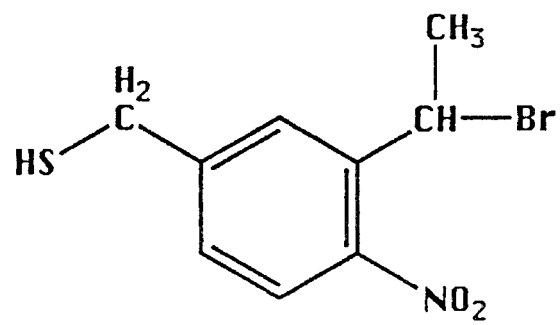
FIG. 8f is a diagram of a brominated precursor with a sulfhydryl function for the drug-delivery catheter system of this invention.
Figure 8G:
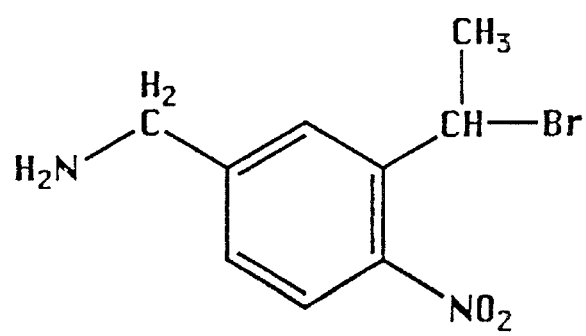
FIG. 8g is a diagram of an alternate example of a brominated precursor with an amine linkage for the drug-delivery catheter system of this invention.

FIGS. 6 and 7 show examples of therapeutic agents 20 utilized in treating or preventing restenosis, the linkers 18 being a platelet adhesion inhibitor such as dipyramidamole (Persantin), or an smooth muscle cell proliferation inhibitor such as an antisense oligodeoxynucleotide (ODN) synthetic fragment (e.g., positions 4–22 of the proto-oncogene c-myb.) (SEQ ID NO: 2) In the case of dipyramidamole, one of the four hydroxyls is coupled in the 1-ethyl position displacing the hydrazine, whereas with the antisense oligodeoxynucleotide fragment the 5'phosphate of the 16-mer nucleotide is coupled in the same position. Each of the therapeutic agents 20 is coupled to a Branched chain-Polymer complex 24 (BPol) such as a star-polymer complex that forms the substrate 16.

Alternative Photolytic Linkers

In some applications it may prove easier to work with the amine groups directly on the natural plastic surface 14 of the catheter body 12 rather than create a maleimide surface for the substrate layer 16. In that event, when a sulfhydryl heterobifunctional linker 18 is employed, it is preferable to prepare an aminomethyl compound after the bromination step by reacting the product with anhydrous ammonia to convert the bromine to an amine. In this case, with either the conversion subsequently to the chlorocarbonyl or the hydrazide and then the therapeutic agent 20, the linker 18 -therapeutic agent 20 complex can be attached to the substrate layer 16 by either crosslinking with glutaraldehyde, or the homobifunctional agent disuccinimidal suberate (DSS) available from Pierce Chemical of Rockford, Ill. The order of the assembly or bonding attachment will depend on the nature and solubility of the material forming the catheter body 12 and the presence of competing groups on the therapeutic agent 20.

Another alternative to the sulfhydryl approach is to use the compounds created by solid phase synthesis of protected peptides, such as 3-nitro-4 bromomethylbenzoic acid, as discussed by Rich, D. H. and Gurwara, S. K., *Preparation of a New o-Nitrobenzyl Resin for Solid-Phase Synthesis of tert-Butyloxycarbonyl-Protected Peptide Acids,* J Am. Chem. Soc. 97:1575–1579 (1975), U.S. Pat. No. 4,062,746 to Rich, and Atherton, E. and Sheppard, R. C., *Solid Phase Peptide Synthesis: A Practical Approach,* p. 71 (IRL Press 1989). The starting material in such a case is a benzoic acid derivative from which the heterobifunctional agent 3-nitro-4 bromomethyl benzoic acid is prepared. Subsequently, this compound is coupled to an amine-containing or converted polymer with CDI. This method can be used to derivitize the amine-modified material forming the surface 14 and substrate layer 16, either before or after attachment of a therapeutic agent 20. Several functional groups on a therapeutic agent 20 can be attached directly to the bromomethyl with suitable protection of other reactive moieties, as with synthesizing peptides. Finally, similar schemes using 1 bromoethyl instead of bromomethyl, and converting the bromine to an alcohol followed by oxidation, would produce an acetophenone group that can be further exploited to form the carbonyl chloride or the diazo ethane.

Stacking or Amplification of the Therapeutic Agent and Other Compounds

Referring to FIG. 7, it may be seen that the therapeutic agent 20 can be bonded in a stacked or amplified configuration through the use of a loose lattice or meshwork, thereby accommodating a very high surface density or molecular concentration per unit area. In discrete macromolecular regions the molecules of the therapeutic agent 20 may be generally aligned with one another to increase packing density, with intervening molecules such as alanines being used as spacers to minimize undesirable cross coupling.

In certain cases where there are two functionalities on the support surface 14 (such as nylon), it may be desirable to use a first functionality to co-locate a fluorescent molecule of appropriate characteristics to act as an energy transfer vehicle next to the complex of the photolytic linker 18 and therapeutic agent 20. The purpose of this fluorescent molecule is to absorb the primary light energy and reemit at a more suitable wavelength or geometry for the photolytic process.

Polymer supports can be shown by dye binding to exhibit at least 40–60 nanomoles of functional groups per $cm^2$ of surface. The area "footprint" of various macromolecular structures can be estimated from the molecular weight and Stoke's radius of a known protein (i.e., gamma globulin), and the assumption of a uniform circular molecular footprint. The degree of coupling of two marker proteins to carboxyl-modified polypropylene surfaces 14 plotted against the footprints provides an estimate of the amount of minimum coupling expected for a peptide of 1000 Dalton molecular weight. Plotting surface concentration against molecular footprint in a logarithmic scale from 100 to 100,000 nmol/cm$^2$ and within a range of zero to 80 nm$^2$ per molecule, yields a generally uniform decreasing curve.

On a dilation balloon having an area of 2 cm$^2$, a minimal surface concentration of 32 nmols could be expected. Using a film of liquid having a 0.05 cm thickness after the inflation or distention of the balloon, the volume for a released therapeutic agent 20 such as a peptide would be 0.1 ml and the peptide concentration would be 320 nmol/ml. This is equivalent to 0.32 mM or 32 micrograms total of biologically active material.

It is also possible to estimate the parameters for effective laser light energy required to accomplish the release given specific combinations of materials using analytical similar to that discussed by McCray, J. A. and Trentham, D. R., *Properties and Uses of Photoreactive Caged Compounds,* Ann. Rev. Biophys. Chem. 18:239–270 (1989). For example, the known light energy required to release 2 mM of adenosine triphosphate (ATP) in 0.01 ml solution from a 2-nitro benzyl compound is on the order of 20 millijoules. This corresponds to $3.4 \times 10^{19}$ photons being required to release $1.2 \times 10^{17}$ molecules. While this is only a 0.05% efficiency ratio, a 20 milliwatt pulse of 1 second duration can easily be achieved using conventional medical lasers, and the peptide discussed above has a concentration that is an order of magnitude less than for ATP.

While representative examples of the preferred embodiments of the above catheter system 10 have been described in detail with reference to the Figures, it is understood that various changes and adaptations may be made in the catheter system 10 and its method of preparation and use without departing from the spirit and scope of the appended claims.

---

What is claimed is:

1. A catheter for applying a therapeutic agent to a tissue site by selectively releasing said therapeutic agent in response to light energy emanating from a source and conducted through at least a portion of said catheter, said catheter comprising:
 a catheter body, said catheter body having a surface including a substrate layer; and
 a linker layer, said linker layer being chemically bonded to said substrate layer with the therapeutic agent being chemically bonded to said linker layer, the therapeutic agent being selectively released from said substrate layer by a photolytic chemical reaction occurring in response to exposure to the light energy emanating from the source and conducted through the portion of the catheter.

2. The catheter of claim 1 wherein the catheter body is a conventional medical catheter selected from the group including: a percutaneous transluminal angiography (PTA) catheter, a percutaneous transluminal coronary angioplasty (PTCA) catheter, a vascular catheter, a peripheral vascular catheter, a thrombectomy catheter, an embolectomy catheter, a renal catheter, a esophageal catheter, a perfusion catheter, an upper gastrointestinal catheter, a lower gastrointestinal catheter, a bile duct catheter, a pancreatic duct catheter, a urethral catheter, a ureteral catheter, and a urogenital catheter.

3. The catheter of claim 1 wherein the catheter body is a fiber optic probe.

4. The catheter of claim 3 wherein the probe is a central nervous system probe.

5. The catheter of claim 1 wherein the catheter body defines a lumen.

6. The catheter of claim 1 wherein the at least a portion of the catheter body is fabricated from a polymer selected from the group comprising: a polyethylene terephthalate, a polyethylene, a polyamide, a polyester, a polyolefin, a polypropylene, a polyurethane, a polystyrene, a polysulfone, and a latex.

7. The catheter of claim 6 wherein the polymer from which the catheter body is fabricated defines the surface of the catheter.

8. The catheter of claim 7 wherein the polymer defining the surface of the catheter is derivatized to form the substrate layer.

9. The catheter of claim 1 wherein the substrate layer has an exposed functional group selected from the group comprising: a carboxyl, an amine, an hydroxyl, a sulfhydryl, a succinimide, and a maleimide.

10. The catheter of claim 1 further comprising:
 a molecular lattice, said molecular lattice being disposed between and chemically bonded to the substrate layer and the therapeutic agent.

11. The catheter of claim 10 wherein the molecular lattice includes at least one branched chain, a bond to the substrate layer, and a plurality of bonding sites to which a plurality of molecules of the therapeutic agent are selectively bonded.

12. The catheter of claim 10 wherein the molecular lattice is a branched polyamino acid including a plurality of amino acids, said amino acids being selected from a group comprising: a lysine, a cysteine, a glutamic acid, an alanine, and an aspartic alanine.

13. The catheter of claim 10 wherein an ancillary compound is bonded to the molecular lattice in addition to the therapeutic agent.

14. The catheter of claim 13 wherein the ancillary compound is a fluorescent marker compound.

15. The catheter of claim 1 wherein the linker layer is formed from a heterobifunctional agent.

16. The catheter of claim 15 wherein the heterobifunctional agent is covalently bonded to the therapeutic agent.

17. The catheter of claim 15 wherein the linker layer is formed from a 2 nitro benzyl compound.

18. The catheter of claim 15 wherein the substrate layer has an exposed functional group, the heterobifunctional agent being bonded to said exposed functional group, the heterobifunctional agent further including an aromatic ring having a nitro group, said nitro group being disposed in an ortho position relative to a methyl group or an ethyl group, said methyl group or said ethyl group being functionalized to accept a complementary bond to the therapeutic agent.

19. The catheter of claim 18 wherein the methyl group or the ethyl group are selected from the group comprising: a methyl, an ethyl, an amino methyl, a 1-amino ethyl, a bromo methyl, a 1-bromo ethyl, a methyl hydrazone, a methyl hydrazine, a 1-ethyl hydrazone, a 1-ethyl hydrazine, a chlorocarbonyl methyl, and a 1-chlorocarbonyl ethyl.

20. The catheter of claim 15 wherein the linker layer is formed from a 2-nitro phenyl compound including an aromatic ring having an ortho position, a meta position, and a para position, a nitro phenyl group being disposed in said ortho position, said 2 nitro phenyl group having a first functionality, said 2-nitro phenyl compound having a second functionality disposed at said meta position or said para position.

21. The catheter of claim 1 wherein the therapeutic agent is selected from a group comprising: a peptide, a protein, a carbohydrate, asteroid, a lipid, a nucleotide, an antisense nucleotide, a peptide fragment, a nucleotide fragment, and an antisense nucleotide fragment.

22. The catheter of claim 1 wherein the therapeutic agent is an antisense oligodeoxynucleotide.

23. The catheter of claim 1 wherein the therapeutic agent is a peptide fragment hirudin (54–65).

24. A method for applying a therapeutic agent to a tissue site, said method comprising the steps of:

provided a catheter having a catheter body and a surface including a substrate layer;

connecting a linker layer and the therapeutic agent to said substrate layer, said linker layer being chemically bonded to said substrate layer, the therapeutic agent being chemically bonded to said linker layer;

positioning at least a portion of said catheter body to which the therapeutic agent connected generally proximate to the remotely located tissue site; and applying light energy to said substrate layer or said linker layer such that the therapeutic agent is selectively and responsively released from said substrate layer by a photolyric chemical reaction occurring in response to exposure to said light energy.

* * * * *

SEQUENCE LISTING ( 1 ) GENERAL INFORMATION:

( i i i ) NUMBER OF SEQUENCES: 2

( 2 ) INFORMATION FOR SEQ ID NO:1

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: unknown ( i i ) MOLECULE TYPE: oligodeoxynucleotide (peptide fragment)

( i i i ) HYPOTHETICAL: No ( i v ) ANTI-SENSE: Yes ( v ) FRAGMENT TYPE: internal fragment ( v i ) ORIGINAL SOURCE: unknown ( v i i ) IMMEDIATE SOURCE: unknown ( v i i i ) POSITION IN GENOME: unknown ( i x ) FEATURE:
        ( A ) NAME/KEY: Hirudin (54-65)

( x ) PUBLICATION INFORMATION: n/a ( x i ) SEQUENCE DESCRIPTION: SEQ ID NO:1

Gly Asp Phe Glu Glu Ile Pro Glu Glu Tyr Leu Gln ( 2 ) INFORMATION FOR SEQ ID NO:2

( i ) SEQUENCE CHARACTERISTICS:
        ( A ) LENGTH: 16 bases
        ( B ) TYPE: nucleic acid
        ( C ) STRANDEDNESS: unknown
        ( D ) TOPOLOGY: unknown ( i i ) MOLECULE TYPE: oligodeoxynucleotide (peptide fragment)

( i i i ) HYPOTHETICAL: No (iv) ANTI-SENSE: Yes (v) FRAGMENT TYPE: internal fragment (vi) ORIGINAL SOURCE: unknown (vii) IMMEDIATE SOURCE: unknown (viii) POSITION IN GENOME: unknown (ix) FEATURE:
  (A) NAME/KEY: Proto-oncogene c-myb (4-22)

(x) PUBLICATION INFORMATION: n/a (xi) SEQUENCE DESCRIPTION: SEQ ID NO:2

GTGTCGGGTC TCCGGC  16